(12) United States Patent
Klefenz et al.

(10) Patent No.: US 8,761,893 B2
(45) Date of Patent: Jun. 24, 2014

(54) DEVICE, METHOD AND COMPUTER PROGRAM FOR ANALYZING AN AUDIO SIGNAL

(75) Inventors: Frank Klefenz, Mannheim (DE); András Kátai, Ilmenau (DE); Gero Szepannek, Dortmund (DE); Tamás Harczos, Vaskut (HU)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 1566 days.

(21) Appl. No.: 11/994,170

(22) PCT Filed: May 10, 2006

(86) PCT No.: PCT/EP2006/004399
§ 371 (c)(1),
(2), (4) Date: Jul. 11, 2008

(87) PCT Pub. No.: WO2007/000210
PCT Pub. Date: Jan. 4, 2007

(65) Prior Publication Data
US 2009/0312819 A1    Dec. 17, 2009

(30) Foreign Application Priority Data

Jun. 29, 2005  (DE) .......................... 10 2005 030 326

(51) Int. Cl.
*A61N 1/05* (2006.01)
*A61N 1/36* (2006.01)
*H04R 25/00* (2006.01)

(52) U.S. Cl.
CPC ........ *A61N 1/36032* (2013.01); *H04R 2225/43* (2013.01); *H04R 25/505* (2013.01)
USPC .................. 607/57; 607/55; 607/56; 607/137

(58) Field of Classification Search
USPC ......................................... 703/11; 607/55–57
See application file for complete search history.

(56) References Cited

U.S. PATENT DOCUMENTS 4,536,844 A  8/1985  Lyon
4,905,285 A  2/1990  Allen et al.
(Continued)

FOREIGN PATENT DOCUMENTS

JP   61-170824 A   8/1986
JP   2-106020 A    4/1990
(Continued)

OTHER PUBLICATIONS

Shamma et al. "A biophysical model of cochlear processing: Intensity dependence of pure tone responses." J. Acoust. Soc. Am., vol. 80, No. 1, Jul. 1986. pp. 133-145.*

(Continued)

*Primary Examiner* — Allen Porter, Jr.
(74) *Attorney, Agent, or Firm* — Keating & Bennett, LLP

(57) ABSTRACT

A device for analyzing an audio signal to obtain an analysis representation of the audio signal includes a converter for converting the audio signal into a representation representing a neurotransmitter vesicle occurrence in clefts between a plurality of nerve fibers and inner auditory cells of an ear model, and a calculator for calculating a neural activity pattern over time on the plurality of nerve fibers, which results based on the neurotransmitter vesicle occurrence, wherein the neural activity pattern is an analysis representation of the audio signal. The inventive device thus generates an especially suitable analysis representation of an audio signal in which masking effects occurring in the generation of action potentials on nerve fibers are considered. The inventive analysis representation is also suitable for an examination of the audio content and also for controlling cochlea implants.

9 Claims, 30 Drawing Sheets

(56) References Cited

U.S. PATENT DOCUMENTS

| | | | |
|---|---|---|---|
| 4,980,918 | A | 12/1990 | Bahl et al. |
| 5,381,512 | A | 1/1995 | Holton et al. |
| 5,388,182 | A | 2/1995 | Benedetto et al. |
| 6,064,913 | A | 5/2000 | Irlicht et al. |
| 2003/0171786 | A1 | 9/2003 | Blamey et al. |
| 2006/0217784 | A1 | 9/2006 | Kitazawa et al. |

FOREIGN PATENT DOCUMENTS

| | | |
|---|---|---|
| JP | 2004-500788 A | 1/2004 |
| WO | 01/99470 A1 | 12/2001 |
| WO | 02/084539 A2 | 10/2002 |
| WO | 03/067514 A2 | 8/2003 |
| WO | 2005/013870 A1 | 2/2005 |

OTHER PUBLICATIONS

Heinz et al.: "Using a Physiological Ear Model for Automatic Melody Transcription and Sound Source Recognition", 114th Convention. Audio Engineering Society Amsterdam, The Netherlands, Mar. 22-25, 2003, pp. 1-12.

Irino et al.: "Segregating Information about the size and shape of the vocal tract using a time domain auditory model: The Stabilised Wavelet-Mellin Transform," Elsevier—Journal for Speech Communication 36, 2002, pp. 181-203.

Bruckmann et al.: "A neural net for 2D-slope and sinusoidal shape detection," (CIST International Scientific Journal of Computing, ISSN 1727-6209).

Sumner et al.: "A revised model of the inner-hair cell and auditory nerve complex," (Journal Acoustic Society of America, vol. 111, No. 5, Pt. 1, May 2002), pp. 2178-2188.

Neher et al.: "Estimating Transmitter Release Rates from Postsynaptic Current Fluctuations" (The Journal of Neuroscience, Dec. 15, 2001, 21(24): pp. 9638-9654).

Greenberg et al.: "A Space-Time Theory of Pitch and Timbre Based on Cortical Expansion of the Cochelar Traveling Wave Delay," XIth International Symposium on Hearing, Grantham.

Official communication issued in counterpart International Application No. PCT/EP2006/004399, mailed on Oct. 2, 2006.

Official Communication issued in corresponding U.S. Appl. No. 11/172,605, mailed on Aug. 12, 2010.

Seneff, "A Computational Model for the Peripheral Auditory System: Application to Speech Recognition Research", ICASSP 86, pp. 1983-1986, 1986.

\* cited by examiner

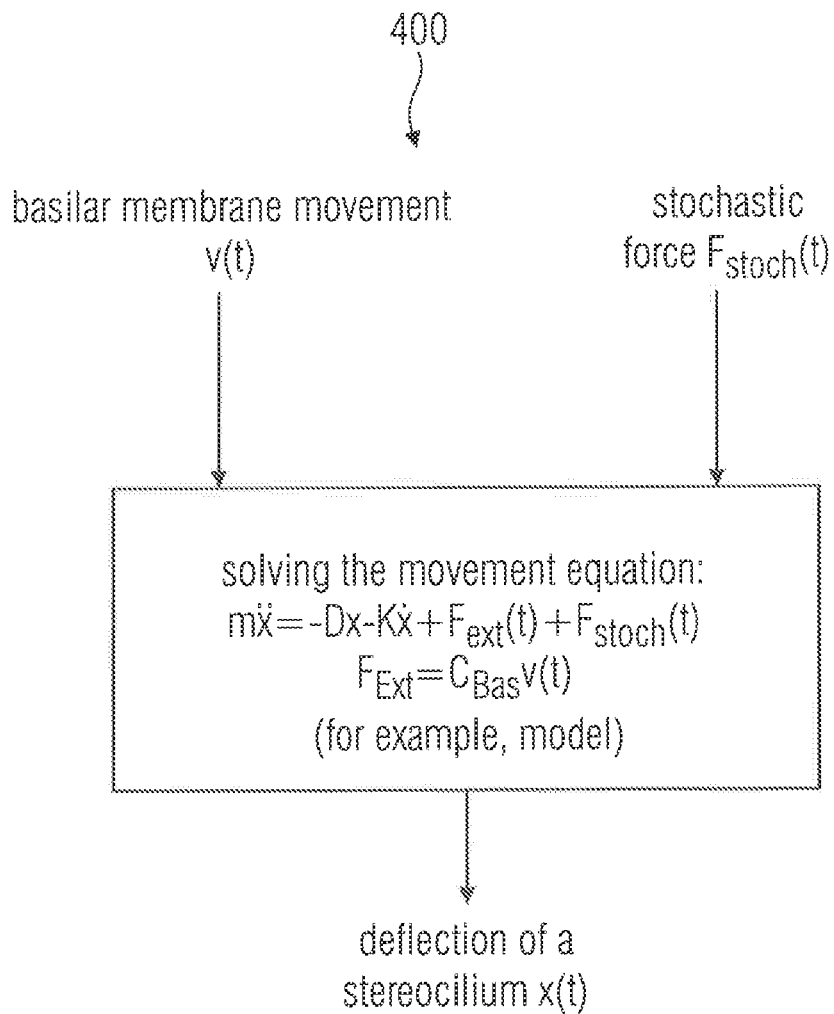

400 basilar membrane movement
v(t)

stochastic
force $F_{stoch}(t)$ solving the movement equation:
$m\ddot{x} = -D\dot{x} - Kx + F_{ext}(t) + F_{stoch}(t)$
$F_{Ext} = C_{Bas}v(t)$
(for example, model)

deflection of a
stereocilium x(t)

m: effective mass of a stereocilium
D: effective spring stiffness constant of the stereocilium
k: constant for the laminar flow resistance of the stereocilium
$C_{Bas}$: constant for the excitation of the stereocilium based on
   the basilar membrane movement

FIG. 4

Detail of chochleogram shows fine temporal and spatial structure in model response to a vowel /i/ (left) and to an inharmonic tone complex of 700, 900, and 1100 Hz (right). Compare the patterns within the pairs of intervals indicated by the vertical lines Training Patterns nine sines of different frequencies illustration 3.1: auditory periphery illustration 3.2:
Outer Ear transmission function-
cylindical surface
illustration of the amount
response as a function of the
azimuth angle on a radial axis Illustration 3.2.: scheme of middle ear and rolled out cochlea illustration 3.4: auditory face illustration 3.5: section of the cochlea illustration 3.6: scheme of the hair cell a) hydromechanics of the inner ear
b) printed circuit of a)
c) non-linear feedback of the outer hair cells

DEVICE, METHOD AND COMPUTER PROGRAM FOR ANALYZING AN AUDIO SIGNAL

TECHNICAL FIELD

The present invention generally relates to a device, a method and a computer program for the analysis of an audio signal in order to obtain an analysis representation of the audio signal, and in particular to a device, a method and a computer program for a neurophysiologically parameterized simulation of the first stages of the hearing system.

BACKGROUND

The analysis and modeling of the human audio system have for a long time formed a main area both in recognizing and classifying audio signals and in medical technology. At that, in particular the setup of the human ear has been studied for a long time. In order to enable an understanding of the present invention, in the following some basic findings regarding the fundamentals of auditory perception are presented.
Physiology: Auditory Periphery and Central Audition The physiological circumstances of the human auditory periphery have meanwhile been researched well and may be looked up in a plurality of scientific documents. Thus, at this point only the main basic facts necessary for the further understanding of later explanations are to be presented.

The peripheral sound processing apparatus of man (see FIG. 20) consists of the totality of outer ear, middle ear and inner ear. Through the acoustic meatus, the sound reaches the eardrum and is passed on in the middle ear via the ossicles. A subsequent processing in the inner ear causes a frequency-dependent transduction of mechanical oscillations into neural nerve action potentials and passing the same on to the connected auditory nerve fibers.
Outer Ear:

The outer ear forms a funnel leading the incoming sound waves to the eardrum. The auricle, the auditory canal, the form of the scull and shoulder modify the sound signal.

As the auditory canal (including auricle) is open at one end and closed at the other, it is physically approximately considered as a half-open tube. Thus, in the case of resonance, i.e. when a quarter of the sound wavelength corresponds to the effective auditory canal length, a sound pressure level gain may be observed. In the resonance maximum at approximately 2500 Hz, the amplification is up to 20 dB. A second resonance ("Cavum Conchae resonance") is caused between 2000 Hz and 2500 Hz by the auricle alone.

Depending on the sound incident direction, as a result of the shape of the outer ear by so called "direction-determining bands" individual narrow frequency ranges are boosted or lowered, respectively. By this, up to a certain measure, the localization of incoming sound is also possible without binaural time and intensity differences, in particular in the vertical plane (median sagittal plane).

The described phenomena may be summarized by the outer ear transfer function (or "head related transfer function" HRTF, respectively), illustrated in FIG. 21.
Middle Ear:

The main task of the middle ear (MO) consists in adapting the sound characteristic impedance of air and of the liquids within the inner ear. If such a functionality is missing, like in the case of sound transmission hearing disability up to 98% of the incoming sound energy is reflected. With a healthy middle ear, around 60% of the signal intensity may be passed on to the inner ear. The sound pressure amplification necessary for this is made possible by the lined up coupling of eardrum, the three ossicles (hammer, anvil and stapes) and the oval window as a contact location to the inner ear (see FIG. 22).

Three different mechanisms are responsible for this impedance transformation:
1. Area ratio of eardrum AT and stapes sole plat AS:

$$\frac{A_T}{A_S} \cong 17$$

2. Ratio of the lever arms of hammer $l_H$ and anvil $l_A$:

$$\frac{l_H}{l_A} \cong 1,3$$

3. Lever arm by the curvature of the eardrum and the asymmetrical suspension of the hammer:

$$F_T \approx 1,4$$

The overall amplification is calculated to be:

$$\frac{p_{ges}}{p_T} = F_T \frac{A_T}{A_S} \frac{l_H}{l_A} \cong 30 \text{ dB}$$

(pT: sound pressure at the eardrum).

The importance of the transfer function of the MO is remarkable, acting like a band pass filter having a wide passband. In the low frequency range it is limited by the mechanical characteristics of eardrum and oval window. With high frequencies, the moments of inertia and friction and bending losses of the ossicles limit the transmission. If the course of the MO transmission function is compared to that of the hearing threshold (see FIG. 23), it may be seen that the auditory sensitivity curve is mainly determined by the mechanical characteristics of the middle and outer ear.

An additional task is fulfilled by the muscles of the MO (M. tensor tympanus and M. stapedius, see FIG. 20). By a reflex contraction, the MO stiffness may be increased and thus an attenuation of lower frequencies may be achieved. A limited protection with regard to high levels and a reduction of the perception of self-produced sounds are the consequence.
Inner Ear:

The structure of the inner ear consists of two units. While the vestibular organ represents a component of the system of equilibrium, the setup of the cochlea forms the final part of the auditory periphery (see FIG. 22). Anatomically, the cochlea is equal to a snail shell having two and a half windings. It is separated into the two chambers "scala vestibuli" (SV) and "scala tympani" (ST) (see FIG. 22) containing perilymph liquid by the cochlear partition.

The operation of the cochlea may again be described in two sections. The hydromechanical part is determined by the macro- and micro-mechanical characteristics of the interior of the winding. The actual functional unit for converting the input signals into neural representations is located within the cochlear partition. The scala vestibuli is connected to the middle ear via the oval window (OW). The same oscillates with the movement of the stapes and thus forces the incompressible lymph liquid to elude. The elusion movement is then passed on to the cochlear partition and forms a traveling wave into the direction of the helicotrema (HC), cochlea spike. Due to the continuously changing mechanical characteristics along its extension (mass cover, rigidity, width, etc.) the partition forms frequency-dependent resonances at certain locations. This tonotopical frequency selectivity is also referred to as location theory.

Locations of maximum wave amplitudes may be associated with the characteristic frequencies on the partition, continuously reaching from high frequencies in the area of the oval window (basis of the basilar membrane) to low frequencies at the helicotrema (end or apex, respectively, of the basilar membrane). Via this dispersion characteristic, frequency contents in the incoming audio signal may be split up to a certain extent.

This functionality is supported by the characteristics of the cochlear division wall (see FIG. 24). The same is closed towards the scala vestibuli by the Reissner membrane (RM). The interface to the scala tympani consists of the basilar membrane (BM) including mounted organ of Corti (CO) on whose top side in the longitudinal direction three rows of outer hair cells and one row of inner hair cells are located. These hair cells are again spanned by the tectorial membrane (TM).

In the area in between the endolymph liquid of the scala media is located. When the cochlear partition moves, the tectorial membrane and the organ of Corti get into a relative movement which leads to a deflection of the sensory hairs located on the hair cells. This partially happens by direct contact, partially, however, also by hydrodynamic coupling. The outer hair cells now have the capability to shorten or lengthen, respectively, very quickly depending on the partition oscillation. This leads to an amplification by up to 1000 of the traveling wave amplitudes and provides sharp and distinct oscillation maxima.

Just like the sensory hairs of the outer hair cells, those of the inner hair cells are also deflected by the relative movement of tectorial membrane and organ of Corti. The measured, three-dimensional movement of the cochlea is complicated and was for example determined by Zenner and Gummert at the University of Ulm. As a consequence of this movement, biochemical processes are started causing a transduction of mechanical movements into neural action potentials (see FIG. 25).

In a state of rest, the inner hair cells have a resting membrane potential of about −40 mV and a low potassium concentration. The surrounding liquid of the scala media, however, comprises an unusually high proportion of potassium ions and is positively charged. With a deflection of the sensory hairs into one direction, so called transduction ion channels open, through which an inflow of positively charged potassium ions into the hair cells takes place due to potential equalization. A deflection of the sensory hairs into the opposite direction closes those channels and through ionic compounds into the baso-lateral cell membrane, the original potential may be reestablished. When the channels are open, the changed sensor potential causes an increased release of afferent transmitter substance.

The same diffuses through the synaptic cleft into the direction of the auditory nerve. Depending on the transmitter concentration in the synaptic cleft, the probability of triggering a nerve action potential (NAP) is increased.

Up to a frequency of just about 5000 Hz the release of the transmitter substance is highly synchronous following the deflection of the sensory hairs. Thus, a linear frequency transmission may occur via a time encoding, which is summarized in literature under the term of "phase locking".

Further, reference is also made to FIG. 26, which again shows the anatomy of the auditory periphery. FIG. 26 here shows the conversion or transmission, respectively, of a noise via eardrum and middle ear to the cochlea. The cochlea here enables a spectral analysis of the incoming noise and a conversion of vibrations into neural impulses. The cochlea further comprises nerve cells generating nerve impulses (action potentials), which are passed on via the auditory nerve to the brain.

FIG. 27 again shows in schematical form the mechanism of signal transmission in the human ear. From FIG. 27 it may be seen, that the cochlea 3210 recognizes different frequencies at different locations (location theory). For example, high frequencies (e.g. with a frequency of 20 kHz) are converted into nerve signals at the beginning of the cochlea, while low frequencies (e.g. with a frequency of 20 Hz) are converted into nerve signals at the end of the cochlea. By this, in the cochlea both a spectral analysis of a noise or an audio signal, respectively, may take place, wherein for a predetermined frequency those nerve cells are excited most that are most suitable for a perception of the respective frequency.

FIG. 28 shows the setup of the organ of hearing, wherein reference is also made to the geometry of the basilar membrane. A graphical illustration 3310 here shows that the width of the basilar membrane 3320 increases from the basis of the cochlea towards the end (apex) of the cochlea by a factor of 10.

A graphical illustration 3320 further shows a coupling of an acoustic wave into the cochlea via an oval window 3330. The coupling in via the oval window 3330 generates a traveling wave in the cochlea traveling from the basis 3340 of the cochlea to the apex 3350 of the cochlea and thus deflecting the basilar membrane 3360 of the cochlea. It is to be noted here, that nerve cells which are located closer to the basis 3340 of the cochlea are excited earlier than nerve cells which are located further from the basis 3340 of the cochlea. In other words, the location of the traveling wave as a function of time may be regarded as a trajectory of the traveling wave. The trajectory may of course also be mapped to discrete nerve cells, so that a trajectory also describes in what time sequence several spatially separated nerve cells are excited by a traveling wave.

FIG. 29 shows an exemplary electric replacement model, by the help of which the propagation of sound waves through the cochlea up to the excitation of the inner hair cells may be modeled. The illustrated model is known as the "extended Zwicker model". The model for example describes the hydromechanic of the inner ear and the nonlinear feedback of the outer hair cells. It is noted, however, that the illustrated model is only one of many possible models for calculating the excitation of the inner hair cells.

FIG. 30 describes, in a schematical illustration, the organ of Corti, and FIG. 31 describes the setup of two different types of hair cells.

FIG. 32 shows a detailed schematical illustration of two hair cells. The schematical illustration of FIG. 32 is designated by 3700 in its entirety. With reference to the graphical illustration 3700, here for improving the understanding the chemical processes within an inner hair cell are shortly outlined.

The hair cell 3710 comprises a plurality of stereocilia 3720 having the shape of fine hairs. An excitation or deflection, respectively, of the stereocilia causes the transmittance or conductivity, respectively, of a cell membrane to change, so that positively charged potassium ions 3730 may enter the hair cell. By this, the intra-cellular potential of the hair cells changes, often designated by V(t). Depending on the intra-cellular hair cell potential V(t), positively charged calcium ions 3740 may enter the cell so that the concentration of calcium ions 3740 is increased. The calcium ions then act upon the release of neurotransmitter molecules 3750 into a synaptic cleft 3760 between the hair cell 3710 and a nerve fiber 3770. The release of the neurotransmitter molecules 3750 typically takes place quantized in vesicles of several thousand molecules.

The concentration of neurotransmitters in the synaptic cleft 3760 then changes the potential in the synaptic cleft 3760. If the potential in the synaptic cleft 3760 exceeds a certain threshold value, then finally an action potential in the nerve fiber 3770 is generated.

FIG. 33 for clarifying finally shows the arrangement of a plurality of hair cells in a sensory point of a human cochlea. From the illustration of FIG. 33 it may be seen that one individual hair cell typically comprises a plurality of stereocilia (hairs) and is coupled to a plurality of nerve fibers.

Some approaches already exist to process or identify audio signals, respectively, with reference to the processes in human hearing. For example, Thorsten Heinz and Andreas Brückmann describe in the article "Using a physiological ear model for automatic melody transcription and sound source recognition" presented in the 114$^{th}$ Meeting of the Audio Engineering Society in Amsterdam, The Netherlands in March 2003, an audio signal analysis and modifications of conventional signal processing algorithms which are perception-oriented.

The above-mentioned article describes a simulation of the functionality of the inner ear including the conversion of mechanical vibrations into information about a concentration of a transmitter substance in the clefts of the inner hair cells. The basilar membrane is here separated into 251 regions of uniform width, and each segment is connected to an inner hair cell, wherein the inner hair cell is excited by vibrations of the corresponding section of the basilar membrane. For a pitch recognition, the concentration of the transmitter substance in the clefts of the 251 described hair cells is then analyzed.

To this end, pitch trajectories are formed and segmented. Further, the mentioned article shortly describes the recognition both of a timbre and a melody recognition.

Further, Toshio Irino and Roy D. Patterson describe in their article "Segregating Information about the size and shape of the vocal tract using a time domain auditory model: The Stabilized Wavelet-Mellin Transform" (published in the Elsevier Journal for Speech Communication 36, 2002, pages 181-203) the application of a two-dimensional Mellin transformation to an auditory image. According to the above article, the Mellin transformation generates a Mellin image from the auditory image which is invariant with regard to the size of a vocal tract of a speaker on whose speech signal the auditory image is based.

The above-mentioned article proposes a speech recognition using a so called Mellin image resulting through a spatial Fourier transformation from a size-shape-image. The size-shape-image is, however, according to T. Irino and R. D. Patterson gained from a stabilized auditory image through a plurality of conversion steps.

Further, A. Brückmann, F. Klefenz and A. Wünsche describe in the article "A neural net for 2D-slope and sinusoidal shape detection" (published in the CIST International Scientific Journal of Computing, ISSN 1727-6209) a neural net for pattern recognition. The described neural net may learn straight lines of different slopes or a set of sinusoidal curves of different frequencies and may recognize corresponding patterns after the learning phase. The corresponding neural net thus realizes a Hough transformation and thus enables a recognition of two-dimensional patterns.

SUMMARY

According to an embodiment, a device for analyzing an audio signal to obtain an analysis representation of the audio signal may have a means for converting the audio signal into a representation, which represents a neurotransmitter vesicle occurrence in clefts between a plurality of nerve fibers and inner auditory cells of an ear model, and a means for calculating a neural activity pattern over time on the plurality of nerve fibers, which results based on the neurotransmitter vesicle occurrence, wherein the neural activity pattern is the analysis representation of the audio signal.

According to another embodiment, a method for analyzing an audio signal to obtain an analysis representation of the audio signal may have the following steps: converting the audio signal into a representation representing a neurotransmitter vesicle occurrence in clefts between a plurality of nerve fibers and inner auditory cells of an ear model; and calculating a neural activity pattern over time on the plurality of nerve fibers resulting based on the neurotransmitter vesicle occurrence, wherein the neural activity pattern is the analysis representation of the audio signal.

An embodiment may have a computer program having a program code for performing the above-mentioned method, when the computer program runs on a computer.

Embodiments of the present invention are based on the finding that a neural activity pattern, which describes action potentials on nerve fibers, which are coupled to auditory cells, presents an especially expressive and efficient description of the audio signal. The neural activity pattern is, indeed, very similar to a representation of the audio signal interpreted by the human brain. It was further found that for a realistic determination of the neural activity pattern, a calculation of an occurrence of neurotransmitters quantized in the form of vesicles is advantageous. Only by considering the quantization of neurotransmitters in the form of vesicles, can points of time of the occurrence of action potentials on the nerve fibers forming the neural activity pattern be determined with sufficient accuracy.

Thus, the inventive concept for analyzing an audio signal is substantially different from known solutions, which, for example, only use the concentration of neurotransmitter substances for an analysis of the audio signal. The calculation of the concentration of neurotransmitter substances is easier than the determination of the actual neural activity pattern which arises in nerve fibers coupled to the auditory cells, but an analysis of the audio signal using the neural activity pattern is adapted to the human hearing substantially better than an analysis based on the concentration of the transmitter substances.

Apart from this, it is to be noted that the neural activity pattern carries substantially more precise time information than hitherto used analysis representations (for example, the concentration of the neurotransmitter substance). Thus, the calculation or determination, respectively, of the neural activity pattern, for example, also enables an accurate evaluation of phase shifts between neighboring nerve cells carrying a high information content for humans.

Further, in a calculation of the neural activity pattern based on the neurotransmitter vesicle occurrence, also a masking of excitations of an auditory cell results, which occur during a dead time (refractory time) of the nerve fiber. This is suitable, as thus the resulting amount of data may be reduced. On the other hand, in this masking, despite the decrease of the amount of data, no information relevant for humans is lost, as also in an actual human auditory system, such a masking takes place. Thus, by the use of an inventive device, it may be achieved that an analysis representation of the audio signal is generated, which is in line with processes in the human auditory system.

An analysis representation of the audio signal, which is formed closely following the human hearing, enables an especially efficient evaluation of the audio signal. In an evaluation of the neural activity pattern it may be achieved that all those parts of the audio signal are detected by a downstream means for audio signal detection (recognition), which may also be detected by humans. Conversely, in the neural activity pattern determined in the inventive way, those acoustic events are masked out, which would neither by detectable (perceptible) by a human listener, whereby an amount of data may advantageously be reduced.

Finally, the inventive generation of a neural activity pattern allows an efficient use of neural networks in an audio signal analysis based on the analysis representation, wherein the neural networks may imitate parts of a human brain. The use of the neural activity pattern as an input signal for a corresponding neural network is especially advantageous, as it turned out that it is exactly this use of naturally occurring excitation patterns (for example, of the inventively generated neural activity pattern) which allows the implementation of a neural network in an especially simple structure. This results from the evolutionary optimization of the overall auditory apparatus.

Further, it is to be noted that the neural activity pattern calculated in the inventive way by evaluating a neurotransmitter vesicle occurrence may also serve for an excitation of nerve fibers of a human patient, for example, to give back at least part of the auditory sense back to a hearing-impaired patient. Here, again, the inventive determination of a neural activity pattern is especially advantageous, as according to an embodiment of the invention, action potentials on nerve fibers are calculated in the form of the neural activity pattern, which would also occur in a similar form with a human being. Thus, coupling in the neural activity pattern into nerve fibers of the auditory nerve is possible without a further signal conversion. Therefore, using the inventive device, also patients may be treated whose auditory cells are seriously impaired, as an excitation of the nerve fibers is calculated.

It is of advantage that the means for calculating the neural activity pattern includes a means for calculating a voltage in a nerve cell based on the neurotransmitter vesicle occurrence and a means for deciding about a release of an action potential forming a peak in the neural activity pattern associated with a nerve fiber based on the voltage in the nerve cell. It was found that the voltage in the nerve cell which describes a post-synaptic potential is a substantial criterion for the generation of a peak in a nerve fiber. The use of the voltage in a nerve cell describing a post-synaptic potential thus enables an especially high time accuracy in the calculation of the neural activity pattern. This high time accuracy is, again, advantageous in the determination of phase relationships between activity impulses on neighboring (adjacent) nerve fibers.

It further turned out that it is advantageous to include the dead time of nerve fibers into a simulation. In other words, it turned out to be advantageous to assume a release of an action potential on a nerve fiber in the neural activity pattern only when a preceding release of an action potential on the nerve fiber is longer ago than a predetermined refractory time. From this, a masking of neurotransmitter vesicle occurrences in quick temporal succession results in the generation of the neural activity pattern, whereby the amount of information of the neural activity pattern to be processed is reduced and whereby, consequently, the neural activity pattern provided by the inventive device allows a more efficient analysis of the audio signal than hitherto known concepts.

It is further of advantage that the means for calculating the voltage in the nerve cell based on the neurotransmitter vesicle occurrence comprises a means for determining a neurotransmitter residual concentration, which is implemented to consider the influence of a diffusion of neurotransmitter vesicles in the determination of the neurotransmitter residual concentration. It is further of advantage that the means for calculating the voltage in the nerve cell is implemented to calculate the voltage in the nerve cell depending on the neurotransmitter residual concentration. The consideration of a diffusion of neurotransmitter vesicles thus enables an even more accurate calculation of a point in time in which an action potential is triggered in a nerve fiber. Thus, the precision of the inventive device may further be increased.

Apart from this, it is of advantage that the means for converting the audio signal comprises a means for converting the audio signal into a representation, which describes a movement of a basilar membrane in the ear model, a means for converting the representation describing the movement of the basilar membrane into a representation describing the deflection of a stereocilium of a hair cell coupled to the basilar membrane and a means for converting the representation describing the deflection of the stereocilium into the representation describing the neurotransmitter vesicle occurrence. Such an implementation is of advantage, as thus a neurotransmitter vesicle occurrence may be calculated in a physically and chemically very precise way.

It is further of advantage that the means for converting the representation describing the movement of the basilar membrane into a representation describing the deflection of the stereocilium is implemented to describe the stereocilium by a model of a harmonic oscillator, which comprises a spring return force and an attenuation based on a laminar flow resistance. Thus, in contrast to conventional concepts, in the generation of an analysis signal based on an audio signal, a self-oscillation of the stereocilia may be considered. Therefore, again, an increased accuracy results in a calculation of the analysis representation of the audio signal and a subsequent audio signal analysis. Oscillations of the stereocilia change a potassium concentration in the auditory cell and, thus, change the point in time in which an action potential is triggered in the neural activity pattern.

It is further of advantage that an excitation of the oscillator model which describes the stereocilium takes place by a stochastic thermal force. Thus, also thermal fluctuations, which cause a comparatively high number of action potentials on the associated nerve fibers in some especially sensitive auditory cells in a state of rest, are considered in the generation of the analysis representation. Thus, again, an especially realistic modeling of a human ear results within the scope of a determination of the analysis representation. It was further found that, in particular, also the stochastic excitation of the stereocilia based on a stochastic thermal force may lead to a decrease of the threshold of perception (detection). Thus, an extremely weak acoustic signal, which would hardly be detectable alone by the auditory cells, may in combination with the stochastic thermal excitation distributed stochastically across a large number of auditory cells cause an effect detectable by the auditory cells, as the very weak signal results in a slight shift of the distribution of the stochastic thermal excitation which is detectable based on the large number of auditory cells present in the neural activity pattern.

It further turned out to be advantageous for a constant which describes a spring return force in the deflection of a stereocilium to use a value, which is valid for a mouse or a young rat. It was found that a spring constant between $1 \times 10^{-3}$ Newton/meter and $6 \times 10^3$ Newton/meter results in an analysis signal which is adapted well to a human auditory sensation.

It is further of advantage that the means for converting the audio signal into a representation describing a movement of the basilar membrane includes a means for calculating a mechanical sound conversion in an inner ear, which is implemented to obtain a representation of an excitation of an eardrum of the ear model, a means for calculating a sound transmission via ossicles, which is implemented to obtain a representation of an excitation of an oval window between a middle ear and a cochlea based on the representation of the excitation of the eardrum, a means for calculating an oscillation excitation of the cochlea, which is implemented to determine the oscillation excitation of the cochlea based on the representation of the excitation of the oval window and a means for calculating the movement of the basilar membrane based on the oscillation excitation of the cochlea. Such an implementation is advantageous, as thus, all important effects occurring in a human ear may be modeled in the ear model, so that the analysis signal is a representation of the audio signal, as it might be received by a human brain.

It is further of advantage that the neural activity pattern determined in the inventive way is used for an analysis of an audio signal content of the audio signal. The analysis of the audio signal content of the audio signal may, for example, take place by comparing the neural activity pattern to a reference neural activity pattern stored in a database. Such a database comparison may be realized in an especially simple way, as the neural activity pattern generated according to an embodiment of the invention suppresses the information not necessary in an effective way. Thus, by considering a dead time of a synapse during the dead time (refractory time) no action potentials are generated, so that by the inventive generation of the neural activity pattern, the redundancy in the generated neural activity pattern is especially low. On the other hand, by the inventive determination of the neural activity pattern, points in time in which action potentials occur on the nerve fibers may be calculated especially accurately, which, again, increases the accuracy of the analysis of the audio signal content. The corresponding points in time are characteristic for reactions of the ear to the audio signal and carry an especially high information content.

Further, a pitch of the audio signal may easily be determined based on the neural activity pattern by determining on which nerve fiber an especially high activity is present. The inventively determined neural activity pattern may further be used for speech recognition, wherein, for example, vocals and/or constants may be determined. Apart from this, it is of advantage to store the inventively calculated noise activity pattern as a fingerprint of the audio signal in a database. Here, an especially effective information storage is possible, as the action potential on the nerve fibers forming the neural activity pattern represent a comparatively low amount of information, wherein redundancies which may not be detected by a conventional compression method are already removed by the means for converting the neurotransmitter vesicle occurrence into the neural activity pattern.

Finally, it is also possible that the device for analyzing the audio signal includes a coupling means which is implemented to output the neural activity pattern to a plurality of nerve fibers of a human patient in the form of electrical and/or chemical excitations. Thus, a human patient who, for example, has an auditory impairment, may be excited with the neural activity pattern, so that he has an auditory perception, which is similar to a natural auditory perception. The coupling means may here include a cochlea implant.

It is further to be noted that it is especially advantageous to supply the neural activity pattern calculated in the inventive way to an analysis means, which includes a means for processing the neural activity pattern, wherein the means for processing the neural activity pattern may be implemented to gain a representation which includes a sequence of pieces of time information, which describes a temporal position of successive trajectories, wherein a trajectory includes activity impulses on different nerve fibers based on the same event in the audio signal.

Here, in the calculation of the trajectories, again, the especially high accuracy of the inventive neural activity pattern may be advantageously used, so that the gained time information also comprises a high accuracy. Due to this high accuracy, the time information may be used for a precise characterization of the audio signal.

BRIEF DESCRIPTION OF THE DRAWINGS

In the following embodiments of the present invention are described in more detail with reference to accompanying drawings, in which:

FIG. 4 shows a flow chart of an inventive method for calculating a deflection of a stereocilium based on the basilar membrane movement according to the first embodiment of the present invention;

DETAILED DESCRIPTION

Figure 1:
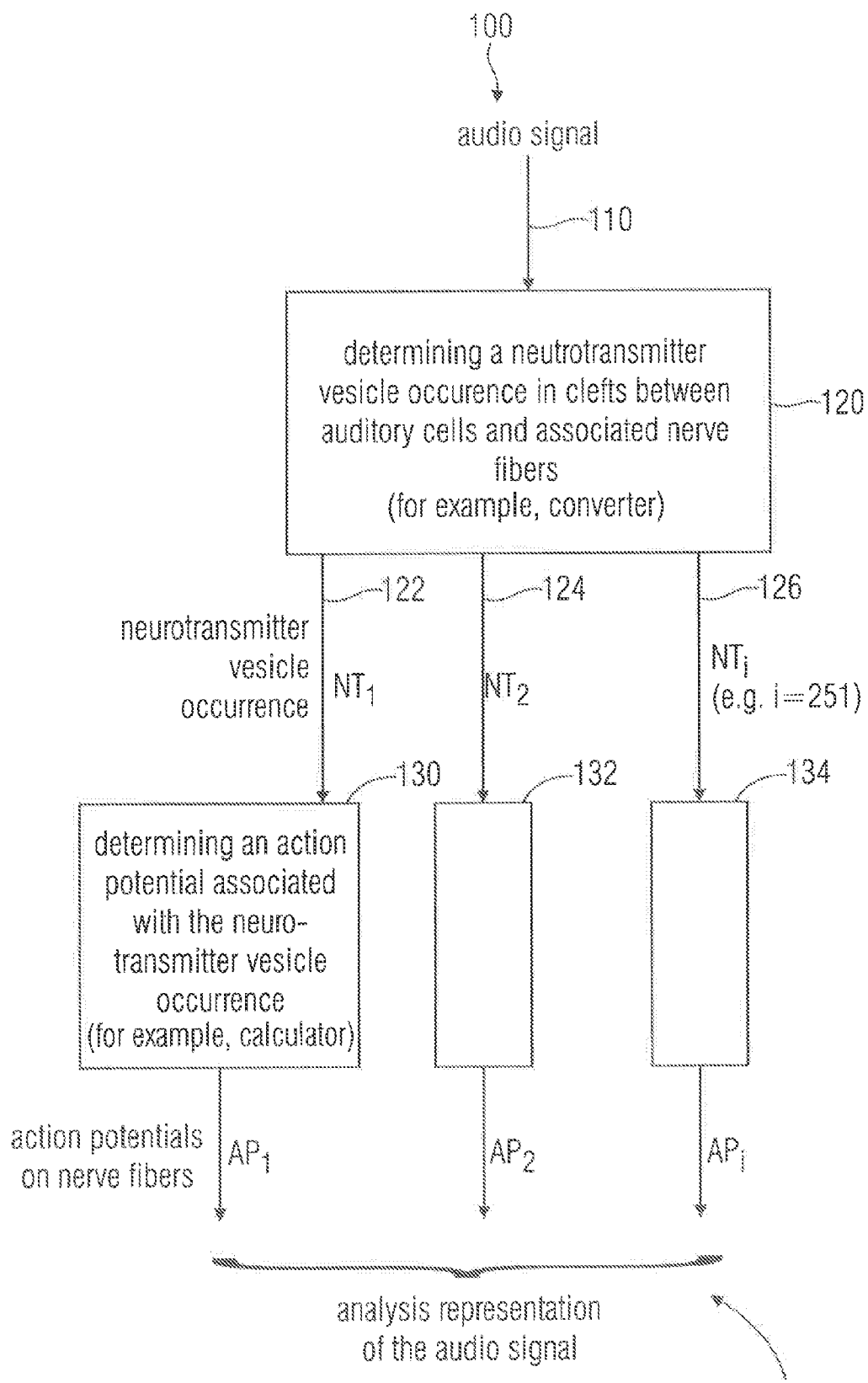
FIG. 1 shows a flow chart of an inventive method for calculating an analysis representation of an audio signal based on the audio signal according to a first embodiment of the present invention.

FIG. 1 shows a flow chart of an inventive method for calculating an analysis representation of an audio signal based on the audio signal according to the first embodiment of the present invention. The flow chart of FIG. 1 is in its entirety designated by 100.

Here, for the audio signal 110 in a first step 120 a neurotransmitter vesicle occurrence is determined in clefts between auditory cells and associated nerve fibers. The occurrence of neurotransmitter vesicles, typically including between one hundred and several thousand neurotransmitter molecules, is determined here for a plurality of auditory cells, wherein it is assumed that the auditory cells are spatially distributed across a model of an ear. It may for example be assumed that the auditory cells considered in the corresponding simulation of the neurotransmitter vesicle occurrence are distributed equidistantly or approximately equidistantly across a cochlea of an ear model. Due to the excitation of the auditory cells by the audio signal, for each of the regarded auditory cells an occurrence of neurotransmitter vesicles may be determined.

Based on the neurotransmitter vesicle occurrence 122 it may then in a second step 130 in a regarded auditory cell an action potential AP1 on a nerve fiber be determined coupled to the respective auditory cell. The indicated proceeding may then be repeated for all auditory cells, which were regarded in the determination of a neurotransmitter vesicle occurrence (steps 132 and 134). Thus, for all auditory cells contributing to the determination of the neurotransmitter vesicle occurrence respectively separately an action potential AP1, AP2, AP3 on a nerve fiber associated with respective auditory cell is calculated based on the respective neurotransmitter vesicle occurrence 122, 124, 126 associated with the respective auditory cell.

In other words, if i auditory cells are considered, then for all i auditory cells an associated neurotransmitter vesicle occurrence 122, 124, 126 is calculated. Based on the neurotransmitter vesicle occurrence then (separately for each nerve fiber) an associated action potential AP1, AP2, AP3 is calculated. Thus, after finishing the calculation, i action potentials are present on nerve fibers together forming the neural activity pattern.

The neural activity pattern AP1, AP2, AP3 thus represents an analysis representation of the audio signal that may be used for a further processing, for example an audio signal recognition.

The inventive method thus provides the advantage that a particularly precise and expressive analysis representation of the audio signal may be formed. The action potentials AP1, AP2, AP3 (that together form neural activity pattern) on the nerve fibers are very similar to those signals that are used by a human brain for a recognition of acoustic events.

In the inventive method in which the action potentials AP1, AP2, AP3 on nerve fibers are derived from the neurotransmitter vesicle occurrence 122, 124, 126 an especially high accuracy may be achieved in a subsequent analysis of the audio signal. The action potentials on the nerve fibers carry accurate temporal information as the action potentials AP1, AP2, AP3 occur quantized. Further, in the determination of the action potentials AP1, AP2, AP3 a dead time (refractory time) occurs which is not considered in known methods for determining analysis representations of an audio signal.

Additionally it is to be noted, that the action potentials AP1, AP2, AP3 may be represented easily due to their quantization, wherein not the height of an action potential but the point in time of the occurrence of an action potential or the rate of the successively occurring action potentials, respectively, carries the information. Also in this respect the inventive method is substantially different from known methods in which for example a concentration of neurotransmitters is evaluated in a synaptic cleft, wherein the concentration represents a continuous curve which does not comprise any temporally drastically defined changes.

Apart from that it is to be noted that the neural activity pattern including simulated action potentials AP1, AP2, AP3 on a plurality of nerve fibers may also be used to excite nerve fibers of an auditory nerve of the human patient who for example has a hearing disorder.

Figure 2:
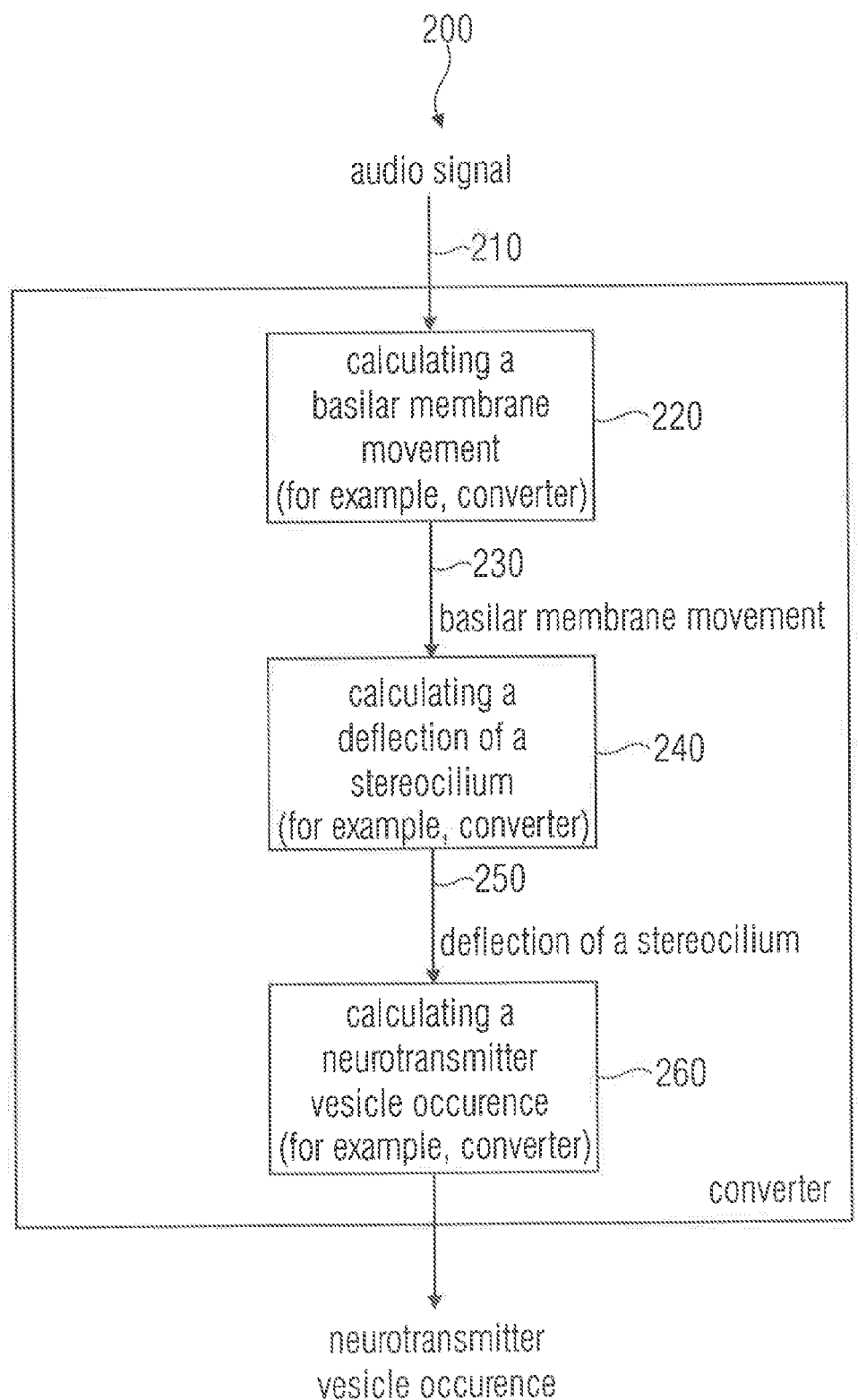
FIG. 2 shows a flow chart of an inventive method for calculating a neurotransmitter vesicle occurrence based on the audio signal according to the first embodiment of the present invention.

FIG. 2 shows a flow chart of an inventive method for calculating the neurotransmitter vesicle occurrence based on the audio signal according to the first embodiment of the present invention. The flow chart of FIG. 2 is referred to as 200 in its entirety. For an audio signal 210 in a first step 220 an associated basilar membrane movement 230 is calculated. In other words, based on the audio signal 210 a movement of a basilar membrane is calculated using an ear model. The movement may for example be described by speed and/or deflection of different points of the basilar membrane. Apart from that it is to be noted that the calculation of the basilar membrane movement is explained in more detail with reference to FIG. 3.

Based on the basilar membrane movement 230, then in a second step 240 a deflection 250 of a stereocilium coupled to the basilar membrane is calculated. The calculation of the deflection of the stereocilium is described in more detail with reference to FIG. 4.

Based on a known deflection 250 of the stereocilium, in a third step 260 the neurotransmitter vesicle occurrence may be calculated or determined, respectively. The calculation of the neurotransmitter vesicle occurrence is apart from that explained in more detail with reference to FIG. 5. Thus, the method shown in FIG. 2 provides a neurotransmitter vesicle occurrence for an audio signal for one or several auditory cells. It is to be noted here, that the basilar membrane movement 230 may be calculated in places in which the regarded auditory cells are located. It is also possible, however, to calculate the overall movement of the basilar membrane, as far as this facilitates an advantageous calculation (for example using an analytic solution).

Figure 3:
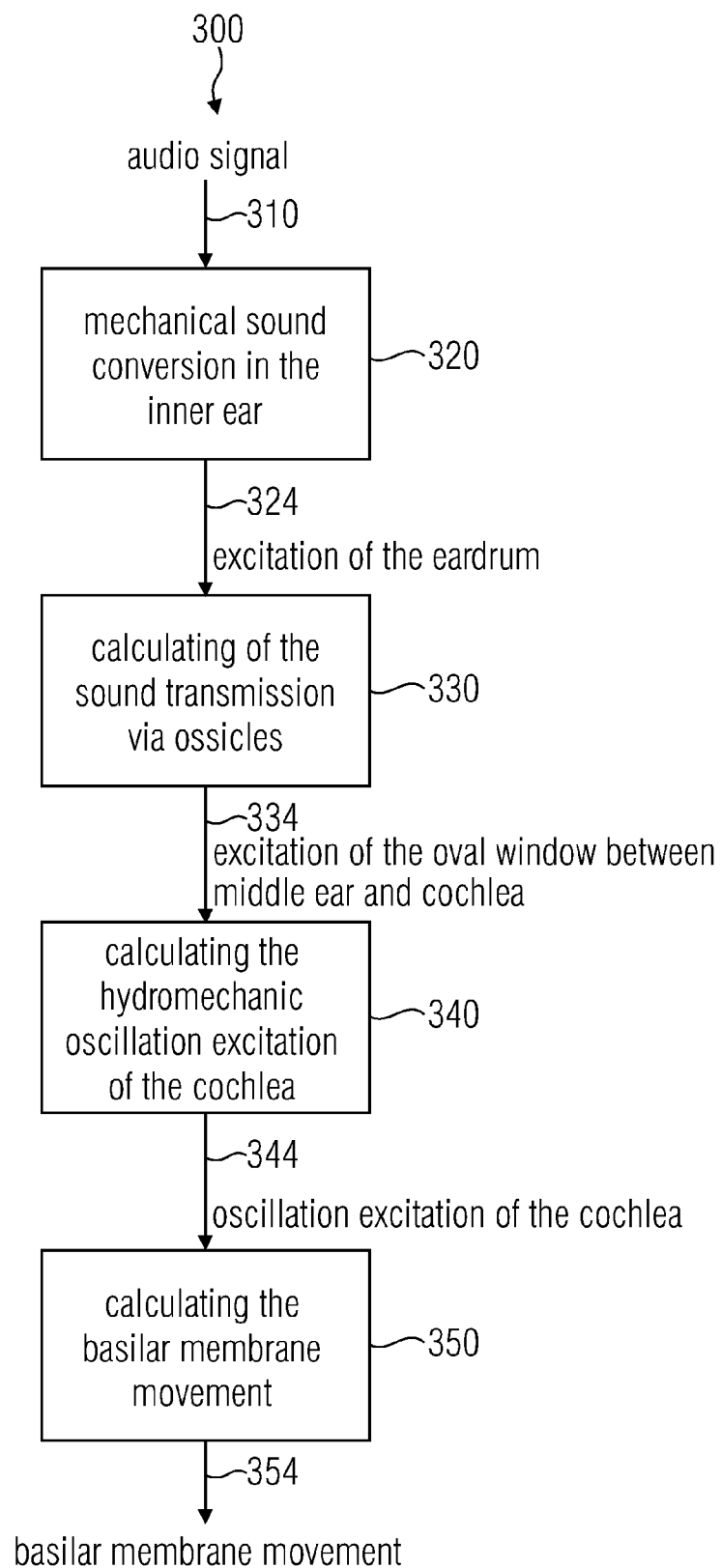
FIG. 3 shows a flow chart of an inventive method for calculating a basilar membrane movement based on the audio signal according to the first embodiment of the present invention.

FIG. 3 shows a flow chart of an inventive method for calculating a basilar membrane movement based on an audio signal according to the first embodiment of the present invention. The graphical illustration of FIG. 3 is designated by 300 in its entirety.

For an audio signal 310 here in a first step 320 a mechanical sound conversion in an inner ear is calculated based on an ear model. Thus, an excitation 324 of the eardrum in the ear model may be determined. So, for example an audio signal 310 may be taken as a basis which impinges on the eardrum. Based on mechanical or fluidical calculations, respectively, thus the excitation of the eardrum may be determined, whereupon the oscillation of the eardrum is known.

In a second step 330 then also the sound transmission via the ossicles of the middle ear in the ear model may be calculated. Here, a detailed mechanical analysis of the middle ear may be performed. It is also possible, however, to only consider force or amplitude transmission ratios, respectively, of the ossicles, whereby a very simple calculation results. It is further possible to additionally consider in the inertia of the ossicles and/or fluidical influences like attenuation. Further, finally for a calculation of the sound transmission via the ossicles it may also be considered that the transfer characteristic of the middle ear may vary depending on the sound intensity. Independent of the complexity of the model which is used for calculating the sound transmission via the ossicles in a second step 330, as a result of the described calculation an excitation 334 of the oval window between middle ear and cochlea may be determined.

Based on the knowledge of the excitation 334 of the oval window between middle ear and cochlea, then in a third step 340 the hydromechanical oscillation excitation of the cochlea may be calculated. This may be performed by a suitable hydromechanical simulation or using a simplified analytical model. Thus, as a result of an analysis of the cochlea, fluidical streams in the cochlea are known or may be determined, respectively.

Based on a knowledge of the oscillation excitation 344 of the cochlea, finally in a fourth step 350 a movement 354 of the basilar membrane may be calculated. Here again linear or non-linear mechanical models may be used. It is noted that a plurality of possibilities exists in order to calculate the basilar membrane movement in selected locations in which the considered nerve cells are arranged.

It is further noted that it is not necessary to explicitly calculate any indicated intermediate variables (i.e. the excitation 324 of the eardrum, the excitation 334 of the oval window or the oscillation excitation 344 of the cochlea). Rather also methods exist to directly approximately infer the movement 354 of the basilar membrane from the audio signal 310. Here, for example a linear or a non-linear filter may be used in order to determine a movement of the given point of a basilar membrane (where advantageously an auditory cell is located). For the calculation of the basilar membrane movement 354 at several locations then a plurality of variously implemented filters may be used. A filter here describes a response of a location of the cochlea as a reaction to the acoustic signal.

Apart from that it is noted, that F. Baumgarte proposed an especially advantageous auditory model for a modeling of the cochlea (F. Baumgarte: "Ein psychophysiologisches Gehörmodell zur Nachbildung von Wahrnehmungsschwellen für die Audiocodierung", ("A physiological auditory model for reproducing thresholds of sensation for audio encoding") Dissertation, University of Hannover, 2000). The model of Baumgarte allows an especially advantageous modeling of the cochlea of an ear model, wherein basic effects, like e.g. a signal reflection at the end of the cochlea, may also be considered.

FIG. 4 shows a flow chart of an inventive method for calculating a deviation of a stereocilium based on the basilar membrane movement. The flow chart of FIG. 4 is designated by 400 in its entirety.

It is assumed here that the movement of the basilar membrane was calculated according to one of the above-mentioned methods (or also in any other way), so that a speed of the movement of the basilar membrane for those locations were nerve cells to be considered are located is known. A deflection x(t) (sometimes also referred to as u(t)) of a stereocilium may be determined by solving a movement equation depending on the basilar membrane movement. The basilar membrane movement is here of course to be considered as a relative movement which may be described by a relative speed v(t). Further, it is of advantage to additionally consider a stochastic force fStOCh(t) for the stereocilium which is caused by an impact movement of the atoms. In other words, it is of advantage to also consider the Brownian movement in the excitation of the stereocilium. Thus, the movement equation of a stereocilium results as an inhomogeneous movement equation of an harmonic oscillator of the following form $$m\ddot{x} = -Dx - K\dot{x} + F_{ext}(t) + F_{stoch}(t)$$

Here, m is the effective mass of the considered stereocilium, D is an effective spring stiffness constant of the stereocilium and K is a constant for a laminar flow resistance of the stereocilium describing the fluidical attenuation of the stereocilium. The excitation of the stereocilium expressed by the external force $F_{ext}$ is proportional to the relative speed v(t) of the basilar membrane movement, so that the following holds true:

$$F_{ext} = C_{Bas} v(t).$$

Here, $C_{Bas}$ is a constant for an excitation of the stereocilium based on a movement of the basilar membrane. As mentioned above, the evaluation of the illustrated movement equation results in the deflection x(t) of the stereocilium which is sometimes also referred to as u(t).

Apart from that it is noted, that also other methods for calculating a deflection of the stereocilia might be used. It is for example possible to use a movement equation of first order modeling a low-pass performance of the stereocilium. In other words, in an alternative specification it may be assumed that a stereocilium represents the low-pass system which may be described by a movement equation of the form $$\tau_c \dot{u}(t) + u(t) = \tau_c C_{cilia} v(t)$$

Apart from that it is to be noted that the consideration of the force Fstoch(t) caused by the Brownian movement is optional.

Figure 5:
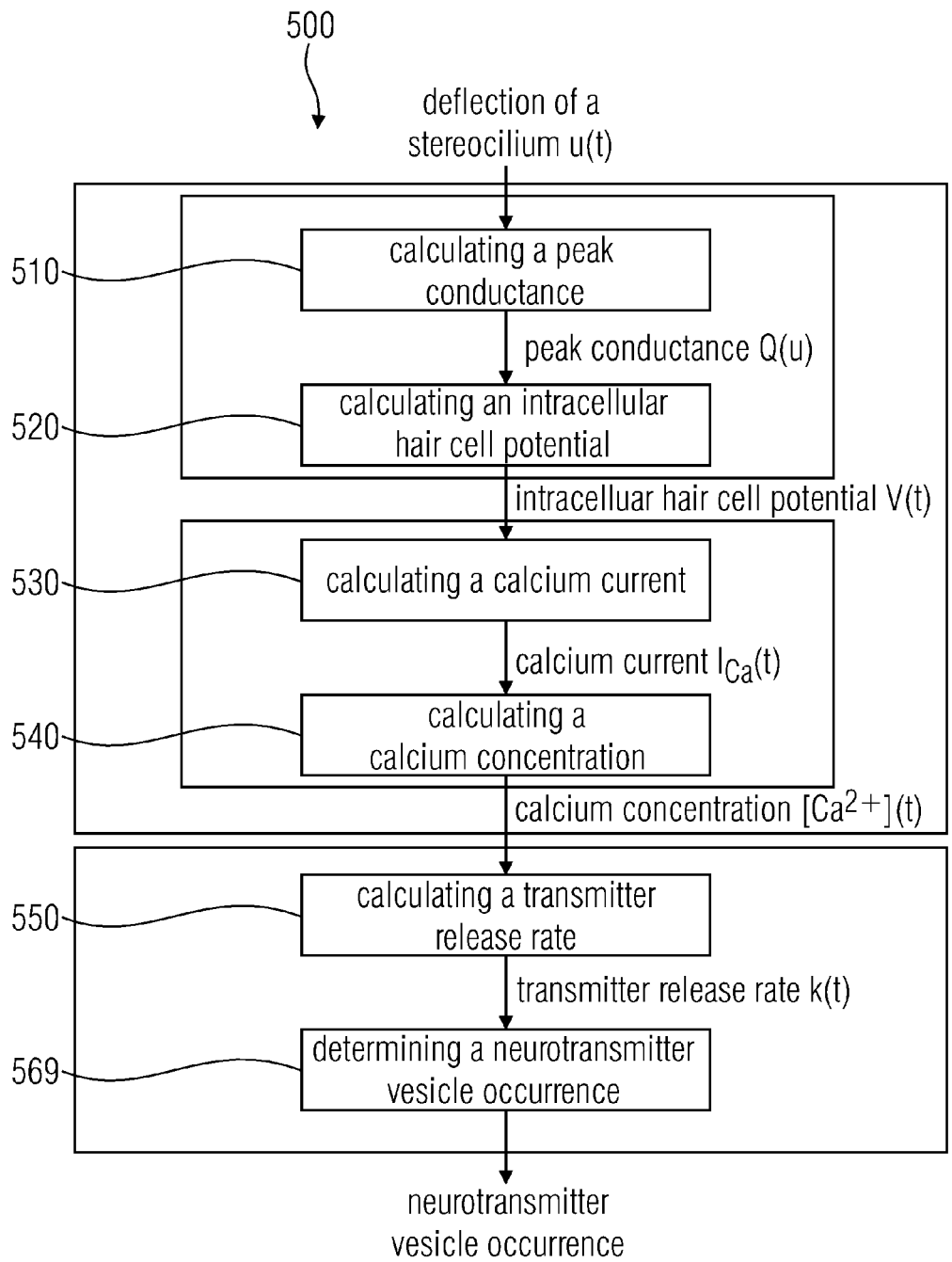
FIG. 5 shows a flow chart of an inventive method for calculating the neurotransmitter vesicle occurrence based on the deflection of a stereocilium according to the first embodiment of the present invention.

FIG. 5 shows a flow chart of an inventive method for calculating a neurotransmitter vesicle occurrence based on a deflection of a stereocilium according to a first embodiment of the present invention. The flow chart illustrated in FIG. 5 is designated by 500 in its entirety.

Based on a deflection u(t) of a stereocilium for example in a first step 510 an apical conductance G(u) may be calculated. A deflection of a stereocilium changes a number of open ion channels, whereby a conductance of a membrane of an auditory cell is changed.

Based on the apical conductance G(u) known from the first step 510 thus in a second step 520 an intracellular hair cell potential V(t) may be calculated. In the calculation of this membrane potential of the cell body for example a model of a passive electric circuit may be used enabling the consideration of a cell capacity. Further, the conductances of different membranes of the auditory cell and the potentials conditional on different ions may be considered.

After a calculation of the intracellular hair cell potential V(t) in the second step 520, then in a third step 530 a calcium current $I_{Ca}$(t) may be calculated. The release of neurotransmitters into the synaptic cleft is conveyed by calcium ions. Here, for example based on the intracellular hair cell potential V(t) a part of open calcium channels may be determined. The calcium current itself is again dependent on the number of open calcium channels and on a potential difference between the intracellular hair cell potential V(t) and an opposed potential for the calcium. Apart from that it is noted that the number of open calcium channels is subject to an inertia which may also be considered.

Based on the calcium current $I_{Ca}$(t) then in a fourth step 540 a calcium concentration $[Ca^{2+}]$(t) may be determined. Here again, for example a low-pass character may be considered, wherein it may be assumed that the calcium concentration takes on a constant value in a state of equilibrium.

Based on the calcium concentration $[Ca^{2+}]$(t) in a fifth step 550 a transmitter release rate k(t) may be determined. Here, the storage of the transmitter substances in a reservoir, in the synaptic cleft and in a processing memory may be considered. Based on the transmitter release rate k(t) in a sixth step 560 coupled to the same an occurrence or a release, respectively, of neurotransmitter vesicles may be determined. It is here of advantage to assume a quantized and stochastic release of neurotransmitter vesicles, wherein a stochastic transport may be described by a function N(n,p). Here, it may for example be assumed, that each of n neurotransmitter quants has an equal release probability in a simulation interval. Apart from that it is noted that also the feedback of neurotransmitters or neurotransmitter vesicles, respectively, in a reservoir may be included into a modeling.

It is further noted that an advantageously usable model of an inner hair cell is described in the article "A revised model of the inner hair cell and auditory nerve complex" of C. J. Sumner, E. A. Lopez-Poveda, L. P. O'Mard and R. Meddis (J. Acoust. Soc. Am., vol. 111, no. 5, Pt. 1, May 2002).

It is further noted, however, that also other models may be used for a calculation of a neurotransmitter vesicle occurrence based on a deflection u(t) of a stereocilium. It has been shown, however, that it is in particular advisory to use a model considering a stochastic release of neurotransmitter vesicles, as such a stochastic release describes a neural activity pattern to be calculated substantially better than models that are based on a continuous or non-quantized release, respectively, of neurotransmitter vesicles. As already mentioned above, apart from that, by an evaluation of the neurotransmitter vesicle release a more accurate information about an audio signal may be obtained in comparison to using continuous release models in which no sharply defined transitions in time take place.

Figure 6:
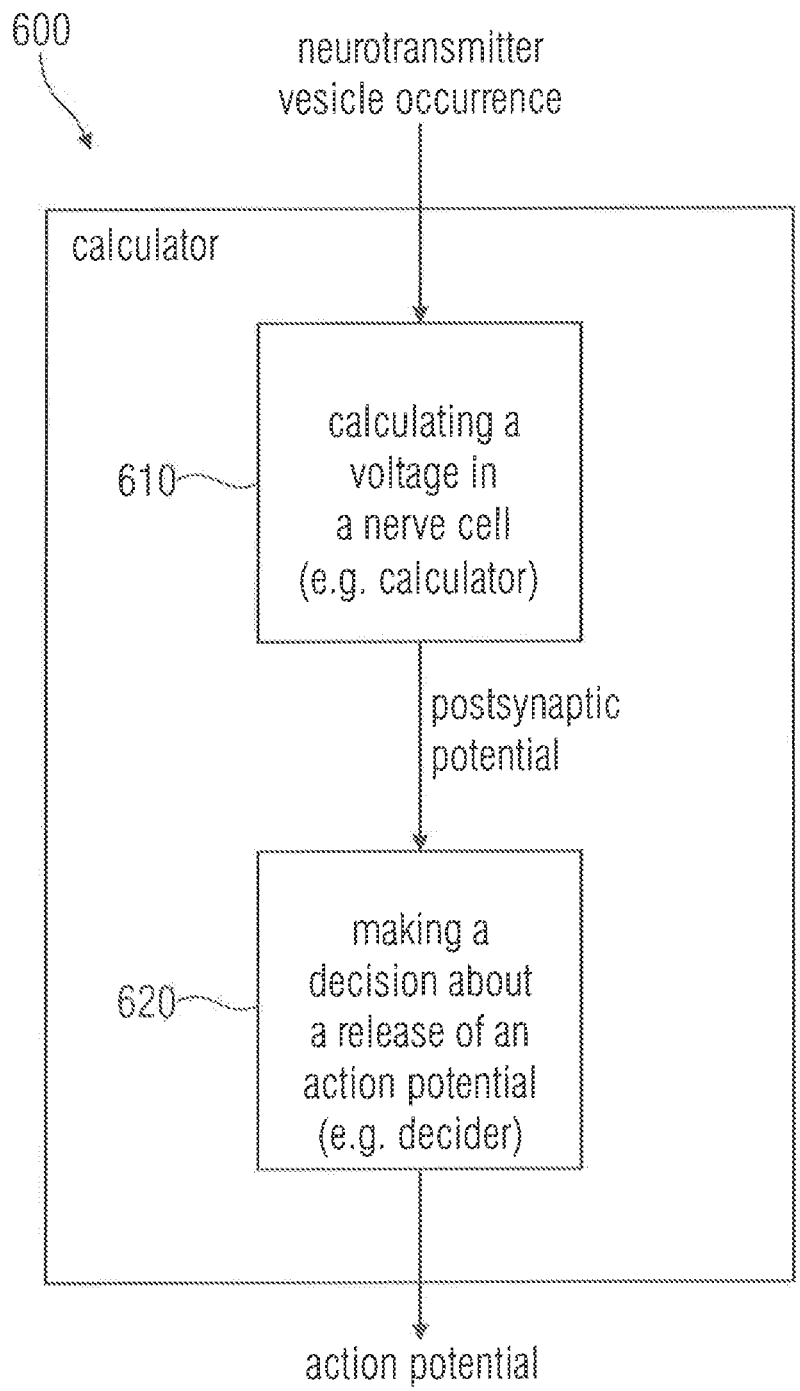
FIG. 6 shows a block diagram of an inventive method for calculating an action potential of a nerve fiber based on the neurotransmitter vesicle occurrence according to the first embodiment of the present invention.

FIG. 6 shows a block diagram of an inventive method for calculating an action potential of a nerve fiber based on a neurotransmitter vesicle occurrence according to the first embodiment of the present invention. The flow chart of FIG. 6 is designated by 600 in its entirety.

In the illustrated method for calculating an action potential based on a neurotransmitter vesicle occurrence, in a first step 610 a voltage in a nerve cell is calculated based on the neurotransmitter vesicle occurrence. This voltage is for example a post-synaptic potential or a depolarization of the post-synaptic nerve cell, respectively. For a calculation of the voltage in the nerve cell for example a diffusion of neurotransmitters may be considered. In other words, an average neurotransmitter concentration may be determined by evaluating a convolution integral, wherein in the convolution integral a diffusion type core may be evaluated. Such a consideration of the diffusion performance is for example described in the article "Estimating Transmitter Release Rates from Postsynaptic Current Fluctuations" by Erwin Neher and Takeshi Sakaba (The Journal of Neuroscience, Dec. 15, 2001, 21(24): 9638-9654). In the calculation of the post-synaptic potential, further a capacity of the cell membrane and membrane-potential-dependent conductivities of membrane ion channels may be considered. In a corresponding model for calculating a voltage in the nerve cell thus an ion exchange through a cell membrane and an excitation by the neurotransmitter is integrated.

Based on the post-synaptic potential calculated in the first step 610, in a second step 620 then a decision about a release of an action potential may be made. Here, it is assumed that by the release of the neurotransmitters the post-synaptic potential is increased.

In summary it may be said: The inner hair cells are the connection between the basilar membranes and the auditive nerve fibers (ANF), sending impulses into the direction of the brain. Before, however, an ANF located at the post-synaptic end may send an action potential towards the brain its voltage has to increase sufficiently and to exceed a threshold value. For this, a chain of events in the pre-synaptic IHC is necessary converting the mechanical oscillations into electrical signals.

At the top end of an IHC hair bundles are located—three rows of stereocilia—connected by so called tip links. They follow the oscillating movement of the basilar membrane—attenuated by the liquid in which they are located and swing back into their original position due to their rigidity. The stereocilia movement may be seen as a system of coupled harmonic oscillators. Simplified, it is described by the following equation:

$$\tau_c \dot{x}(t) + x(t) = \tau C_{cilia} v(t),$$

wherein x(t) stands for the deflection of the stereocilia and v(t) for the speed of the BM. τc is a time constant, $C_{cilia}$ a gain factor. In low frequencies, the stereocilia move in phase with the BM speed, in high frequencies in a phase shifted way.

In the interior of the IHC cell membrane a substantially lower potential is present than in the exterior. This is basically influenced by the present concentration of (positively charged) potassium ions. There is a continuous flow of ions between inside and outside. In a state of rest equilibrium concentrations of [K+]=130 mmol/l (inside) and [K+]=155 mmol/l (outside) are established. It is assumed that also in the state of rest about 15% of the ion channels located at the stereocilia ends are opened. If the stereocilia now move in a medial direction this leads to an opening of additional channels. The conductivity between inside and outside of the IHC is increased. By this, more positively charged potassium ions flow from the outside to the inside and the voltage in the inside of the IHC increases. The other way round, a deflection of the stereocilia in the opposite (lateral) direction inhibits the ion flow and thus leads to a decrease of the membrane potential.

The stereocilia react extremely sensitive to movement. Already a sinusoidal deflection by +/−0.003 degrees is recognized as an audible signal. But also without an external excitation by the oscillating basilar membrane the stereocilia move. They underlie a Brownian movement, so that also completely without any incoming sound waves—depending on the type of the nerve fiber—up to more than 100 action potentials per second are emitted.

A depolarization of the hair cell opens voltage-dependent calcium channels in the cell membrane lying in the proximity of so called active zones. These are regions at the afferent end of the synaptic cleft, in which neurotransmitters are located. From the outside, this way more Ca++ ions may enter the IHC. This inflow of calcium ions leads to the release of neurotransmitters. A high speed in signal transmission is guaranteed by the fact that the messengers are already "packed" in so called vesicles of about the same number of several thousand neurotransmitter molecules and are on call. This may be modeled by so called pools of available vesicles.

The release of the transmitter molecules into the synaptic cleft happens by the fact that the vesicle diffuses at locations of the pre-synaptic membrane provided for this, the active zones, combines with the membrane and releases its content—the neurotransmitters—into the cleft. If the pool of available vesicles becomes empty, that it is gradually refilled again. Further, the use of a reprocessing pool is recommended, in which transmitters from the cleft are packed again with a certain rate to be vesicles and from there directly reach the free pool again. Part of the transmitters is lost in the synaptic cleft.

The release of neurotransmitters from the pool of vesicles is generally described as binominally distributed. The emission probability here is dependent on the calcium concentration inside the IHC cell membrane in the proximity of the active zones.

The original modeling of the voltage course in the nerve cells goes back to Hodgkin and Huxley from the year 1952. Here, basically the exchange of potassium [K] and sodium ions [Na] and a specific "leak" [L] (basically of CL$^-$-ions) are important that distinguish themselves by different maximum conductivities (gNa, gK, gL) and the time course of the membrane permeability depending on the present potential (modeled by the variables m, h, n dependent on u(t)). The membrane voltage u(t) performs according to $$u'C = -\Sigma I_k(t) + I(t)$$

$$\Sigma Ik = (u-VNa)m^3hgNa + (u-VK)n^4gK + (u-VL)gL$$

wherein u' indicates the derivation according to time. VNa, VK and VL are Nernst equilibrium potentials determining the direction of the ion exchange. Ik(t) represents the ion exchange through the cell membrane, I(t), however, is an external current—here e.g. through the neurotransmitters emitted by the IHC—and C is the capacitor formed by the cell membrane. When an external current flows into the cell, the capacitor is charged and a leak through the membrane ion channels results. The time performance of the conductivities depending on the membrane potential is described by a system of three differential equations:

$$m' = \alpha m(u)(1-m) - \beta m(u)m,$$

$$n' = \alpha n(u)(1-n) - \beta m(u)n,$$

$$h' = \alpha h(u)(1-h) - \beta m(u)h.$$

The functions αi(u) and βi(u) depending on the voltage u were adjusted by Hodgkin and Huxley for i={m, n, h}. Differently fast reactions of the different ion flows result upon an external voltage change characterizing the voltage course in the membrane. If now a vesicle diffuses from the pre-synaptic IHC into the cleft, it bonds to a receptor protein of the post-synaptic membrane and releases charge. By the molecules of a vesicle the post-synaptic potential is increased by a thus designated mEPP (miniature end-plate potential) of about 0.5-1 mV.

If the depolarization of the post-synaptic nerve cell described by the post-synaptic potential exceeds a certain threshold value v, then for example the release of an action potential results.

Action potentials are for example characterized by their almost identical time course. The membrane voltage primarily depolarizes extremely strong for a very short period of less than a millisecond, then it hyperpolarizes and is blocked for a period of time in which no further action potentials may occur.

The performance of an auditory nerve fiber i may be described by the points of time of fired spikes $T = \{t_i^k | 1 \le k \le ni\} = \{t | ui(t) = v\}$, wherein ui(t) is the voltage of the post-synaptic membrane i and v is the threshold value necessary for triggering an AP. In general v=v(t) is assumed to be dynamic, as neurons are blocked for a short period directly after the emission of a spike. This spike rejection is generally modeled by means of a short absolute refractory time Tabs followed in about 0.8 ms by a subsequent exponential decay with a time constant τ of about 0.25 ms, so that the threshold value voltage may be modeled by $$v(t) = vo + \sum \eta o e^{\left(\frac{-(t-t_i^{(k)} - \tau_{abs})}{\tau}\right)} * I_{[\tau_{abs}, \infty]}(t - t_i^{(k)}),$$

when the neuron is not in the absolute refractory state and v(t)=∞, if t−t(k)$_i^{(k)}$∈[0, τ$_{abs}$] for a k∈{1, . . . , ni}, with I(·) as an indicator function. For reasons of computational efficiency the sum is usually simplified to the influence of the last 1 or 2 spikes.

In other words, an action potential is triggered when the post-synaptic potential exceeds the predetermined threshold value. This threshold value may vary in time. Apart from that it is noted that in a generation of an action potential advantageously both an absolute refractory time, i.e. a dead time during which a triggering of a further action potential is no more possible, and also a relative refractory time during which a threshold for a triggering of an action potential is higher than in a state of rest, may be considered. The absolute refractory time may here be for example modeled by an infinitely high threshold value v, may also be integrated in another way, however. The relative refractory time may be described by a time-variable threshold value v for the triggering of an action potential.

It may thus be guaranteed that dead times of the nerve fibers are considered in a generation of action potentials or a generation of the neural activity pattern, respectively, describing action potentials on a plurality of nerve fibers. By this, the amount of information of the neural activity pattern may be reduced which enables a further processing of the neural activity pattern and a storage of the neural activity pattern. Apart from that, by a described arrangement also a spontaneous activity of the nerve fibers may be considered.

It is further to be noted that during the absolute refractory time also the occurrence of a plurality of neurotransmitter vesicles overlapping time in does not lead to a triggering of an action potential. In the relative refractory time, however, the occurrence of a single neurotransmitter vesicle does not trigger an action potential, while, however, an overlapping occurrence of several neurotransmitter vesicles in the relative refractory time may well result in a triggering of an action potential.

According to the method described with reference to FIGS. 1 to 6, a particularly expressive analysis representation of an audio signal may be generated including a neural activity pattern. In the inventive manner, the neural activity pattern is calculated based on a neurotransmitter vesicle occurrence, wherein the stochastic nature of the neurotransmitter vesicle occurrence may be considered. Additionally, also in the determination of action potentials on the nerve fibers all relevant effects (like for example the diffusion of neurotransmitters and the potential dependence in the triggering of an action potential on a nerve fiber) may be considered. For this reason, the neural activity pattern calculated in the inventive way comprises a particularly high time accuracy necessary for an expressive analysis. Using a neural activity pattern determined according to the invention, for example also a phase relation between the action potentials of neighboring nerve cells may be evaluated which is conventionally only little expressive due to a modeling which is too imprecise.

It is further noted that it is advantageous to convert neurotransmitter vesicles 1 on 1 into electrical impulses of a size of 1 mV. A calculated release of a neurotransmitter vesicle may for example be used in order to generate a square impulse in a cochlea implant control device and to feed the resulting electric impulses then to a cochlea implant. By the impulses auditory nerve fibers may then be triggered. Here, for example, 251 nerve signals for 251 auditory nerves are for example scaled to the 22 channels typically available in a cochlea implant.

Further, it is of advantage to further process the neural activity pattern to obtain an even more advantageous analysis representation of the audio signal. The calculation of the neural activity pattern may here advantageously take place according to the above-described method, wherein also other methods providing a neural activity pattern may be used for obtaining an improved analysis representation.

Figure 7:
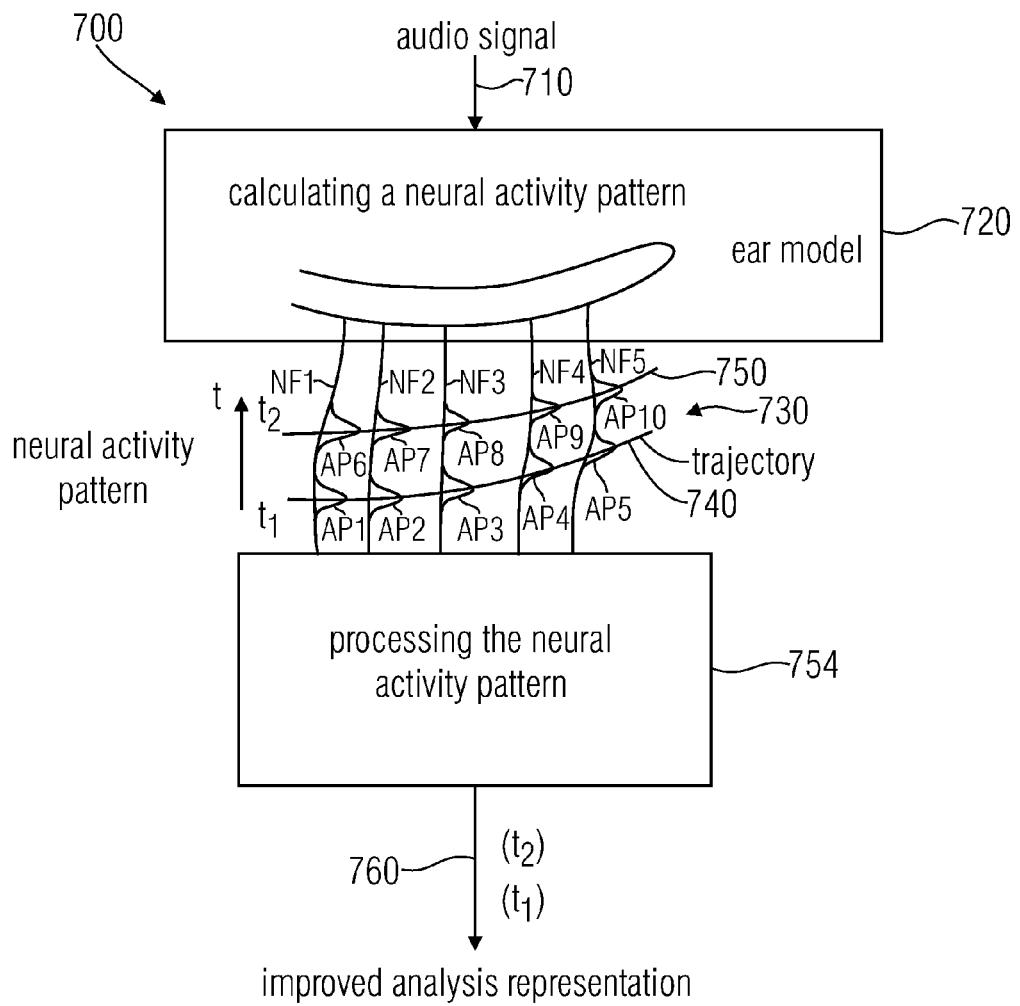
FIG. 7 shows a flow chart of an inventive method for calculating an analysis representation of an audio signal according to a second embodiment of the present invention.

FIG. 7 shows a flow chart of an inventive method for calculating an improved analysis representation of an audio signal according to a further embodiment of the present invention. The flow chart of FIG. 7 is designated by 700 in its entirety. Here, based on an audio signal 710 in a first step 720 a neural activity pattern 730 is calculated. In the determination of the neural activity pattern 730 in the first step 720 for example an ear model may be used as it was already explained in detail above. The result of the calculation of the neural activity pattern 730 is therefore time courses of action potentials on a plurality of nerve fibers NF1, NF2, NF3, NF4, NF5.

It is noted here that the neural activity pattern 730 as a response to the audio signal 710 comprises characteristic trajectories 740, 750. In other words: if an acoustic event occurs in the audio signal 710, then this acoustic event results in a series of action potentials AP1, AP2, AP3, AP4, AP5, occurring slightly offset in time on a plurality of nerve fibers NF1, NF2, NF3, NF4, NF5. A trajectory 740, 750 thus includes a plurality of action potentials AP1, AP2, AP3, AP4, AP5 or spikes, respectively, on several different nerve fibers NF1, NF2, NF3, NF4, NF5 ("pulse spiking trains").

A trajectory 740, 750 is among others characterized by the fact that it may be recognized as a line in a two-dimensional representation of the neural activity pattern 730 over time. The trajectory 740, 750 may here either be straight or curved, wherein different types of curvature (e.g. parabolic or hyperbolic) may occur. Apart from that it is to be noted that it is also possible in some cases to approach a trajectory 740, 750 by a section from a sinusoidal function. It is further to be noted that a trajectory 740, 750 comprises a minimum length according to definition. A trajectory 740, 750 is thus only present when action potentials AP1, AP2, AP3, AP4, AP5 occur on a minimum number of nerve fibers. Here, the action potentials then form a line segment in a two-dimensional representation of the neural activity pattern as a function of time.

Figure 8:
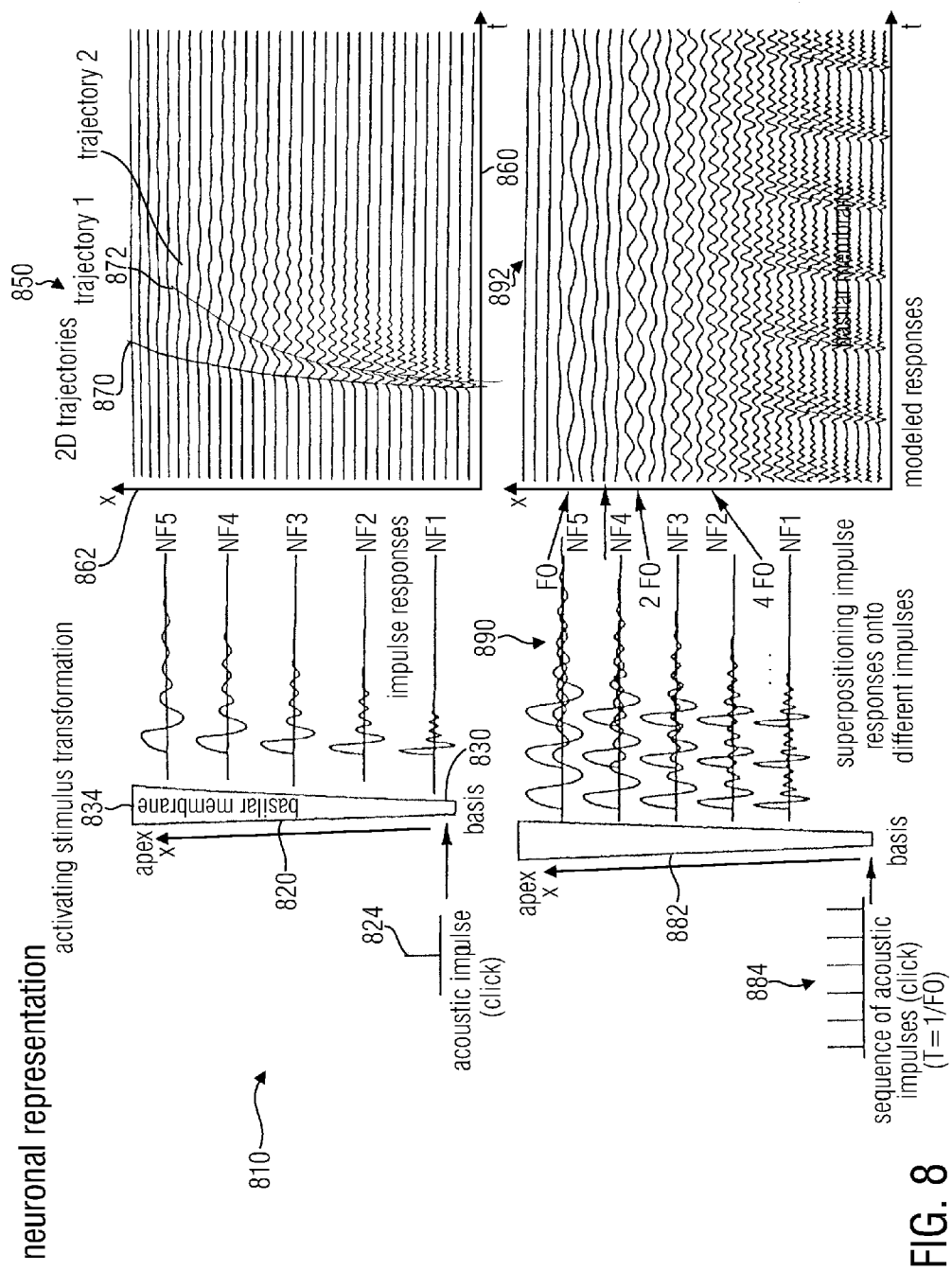
FIG. 8 shows a graphical illustration of exemplary neural activity patterns.

Additionally it is to be noted that a two-dimensional representation of a neural activity pattern 730 as a function of time here describes an illustration in which the action potentials are plotted in parallel on several nerve fibers as a function of time, wherein the time is plotted in the direction of an abscissa, and wherein courses of the action potentials are plotted on several nerve fibers by line trains that are basically parallel to the abscissa (see also FIG. 8). A trajectory 740, 750 is thus present when matching maxima or minima of the action potentials AP1, AP2, AP3, AP4, AP5 in the two-dimensional representation of the neural activity pattern 730 may be connected by a straight or curved line (which may be smooth or free of bends, respectively). A trajectory may thus be regarded as a connecting line of matching minima or maxima of action potentials of neighboring nerve fibers.

The inventive method shown in the flow chart 700 includes in a second step 754 the processing of the neural activity pattern formed in the first step 720. At that, the neural activity pattern 730 may be regarded in a two-dimensional illustration as a function of time and as a function of the position of the nerve fibers. In the second step 754 thus the neural activity pattern 730 is processed in order to obtain a sequence of time information t1, t2 as an analysis representation, describing the temporal location of subsequent trajectories 740, 750. At that it is assumed that a trajectory 740, 750 includes or connects, respectively, activity impulses AP1, AP2, AP3, AP4, AP5 on different nerve fibers NF1, NF2, NF3, NF4, NF5 based on the same event in the audio signal. The determined time information t1, t2 here describes the point in time of the occurrence of the trajectories 740, 750. It is further noted that a trajectory 740, 750 is only recognized when a minimum number of nerve fibers NF1, NF2, NF3, NF4, NF5 comprise an action potential AP1, AP2, AP3, AP4, AP5, whereby it is prevented that individual action potentials in the neural activity pattern are erroneously identified or recognized, respectively, as a trajectory.

An acoustic event bringing a trajectory with it may for example be the beginning of a tone. Also vocals generate at least one characteristic trajectory which may be recognized in the inventive method and which subsequently time information may be associated with. Conventionally, however, a tone even includes several trajectories, wherein advantageously for each of the consecutive trajectories an associated time information may be generated. The time information may here for example designate a starting point in time of the trajectory, i.e. a point in time in which the first nerve fiber NF1, NF2, NF3, NF4, NF5 belonging to the trajectory 740, 750 comprises an action potential AP1, AP2, AP3, AP4, AP5.

The processing of the neural activity pattern 730 may for example be implemented so that such patterns in the neural activity pattern are recognized as a trajectory which are associated with a traveling wave on a basilar membrane of an ear model. In other words, a trajectory may be recognized when an excitation pattern is applied to the individual nerve fibers which is based on a propagation of a traveling wave. A traveling wave here typically triggers action potentials consecutively and with a small but not infinitesimal time offset on the plurality of nerve fibers.

Further, it is to be considered in the above approaches that usually nerve fibers, which advantageously respond to low frequencies according to the ear model, are activated later or comprise an action potential, respectively, as compared to nerve fibers advantageously detecting high frequencies. The reason for this is that auditory nerves which are responsive to high frequencies are arranged at the start of the cochlea or the basilar membrane, respectively, whereas auditory nerves recognizing low frequencies are arranged at the end of the cochlea.

With the propagation of a sound event across the cochlea or across the basilar membrane, respectively, here a frequency-dependent delay results, so that high frequency portions generate an activity potential on the respectively associated nerve fibers earlier than low frequency portions.

Thus, also the illustration of FIG. 7 shows action potentials AP1, AP2, AP3, AP4, AP5 on a plurality of nerve fibers NF1, NF2, NF3, NF4, NF5. It is assumed here that a first nerve fiber NF1 is associated with a high frequency (e.g. 20 kHz), while a fifth nerve fiber (NF5) is associated with a low frequency (e.g. 20 Hz). An intermediate second nerve fiber NF2, a third nerve fiber NF3 and a fourth nerve fiber NF4 are associated with intermediate frequencies.

For a better understanding here also a time axis t is pointed out. It may be seen that the action potential AP1 on the first nerve fiber NF1 occurs earlier than action potentials on the remaining nerve fibers NF2, NF3, NF4 and NF5. The matching action potentials on the five nerve fibers thus form in a time consideration a first trajectory 740 to which an starting point in time t1 may be associated. A later following second acoustic event again generates action potentials AP6, AP7, AP8, AP9, AP10 on the nerve fibers NF1, NF2, NF3, NF4, NF5, forming the second trajectory 750. With the second trajectory 715 then a second point in time t2 may be associated.

It is now the task of the processing of the neural activity pattern in the second step 730 to recognize the first trajectory 740 and the second trajectory 750 and to provide corresponding time information (t1), (t2), associated with the trajectories 740, 750. The pieces of time information (t1) and (t2) thus form an improved analysis representation of the audio signal 710, enabling an even more advantageous processing than the neural activity pattern itself. The improved analysis representation 760 may in particular be also used for the purpose of a speed recognition. Apart from that the improved analysis representation 760 is also very well suitable for a rhythm recognition of a signal.

For a better understanding, FIG. 8 shows an illustration of exemplary neural activity patterns. A first graphical illustration 810 shows how a basilar membrane 820 is excited by an acoustic impulse 824 (CLICK). The acoustic impulse 824 is coupled in via the oval window of the cochlea and thus first reaches a basis 830 of the basilar membrane 820. The acoustic impulse then propagates across the basilar membrane 820 to its apex 834. Along the basilar membrane for example five (auditory) nerves are arranged, wherein a graphic illustration 840 shows pulse responses of the basilar membrane 820 with an excitation by the acoustic impulse 824 at different locations of the basilar membrane. It may be seen here that in the proximity of the basis 830 of the basilar membrane 820 a short impulse response occurs basically including high frequency proportions, while, however, in the proximity of the apex 834 of the basilar membrane 820 a long impulse response occurs basically including low frequencies.

A further graphical illustration 850 shows impulse responses for a plurality of locations along the basilar membrane. An abscissa 860 here describes the time while an ordinate 862 indicates a location along the basilar membrane 820. From the graphical illustration 850 it may be seen that the impulse responses at different locations along the basilar membrane 820, in an excitation by the acoustic impulse 824, comprise a plurality of trajectories of which two trajectories 870, 872 are marked in the graphical illustration 850 as an example. Trajectories which are shown in the graphical illustration 850 of the impulse response of the basilar membrane may apart from that also be identified in a neural activity pattern in a similar way, which is not explicitly shown here.

Apart from that it is to be noted here that the trajectories 870, 872 shown in the graphical illustration 850 comprise a different curvature performance. The different curvature performance results from the fact that in different locations of the basilar membrane 820 different frequencies are dominant (for example at the basis of the basilar membrane high frequencies and at the apex of the basilar membrane low frequencies).

A further graphical illustration 880 shows, analog to the graphical illustration 810, an excitation of a basilar membrane 882 by a sequence of acoustic impulses (CLICKS) designated by 884. Accordingly, a graphical illustration 890 shows a superposition of impulse responses onto different acoustic impulses. A graphical illustration 892 again shows the corresponding impulse response for a large number of locations x on the basilar membrane 881.

Figure 9:
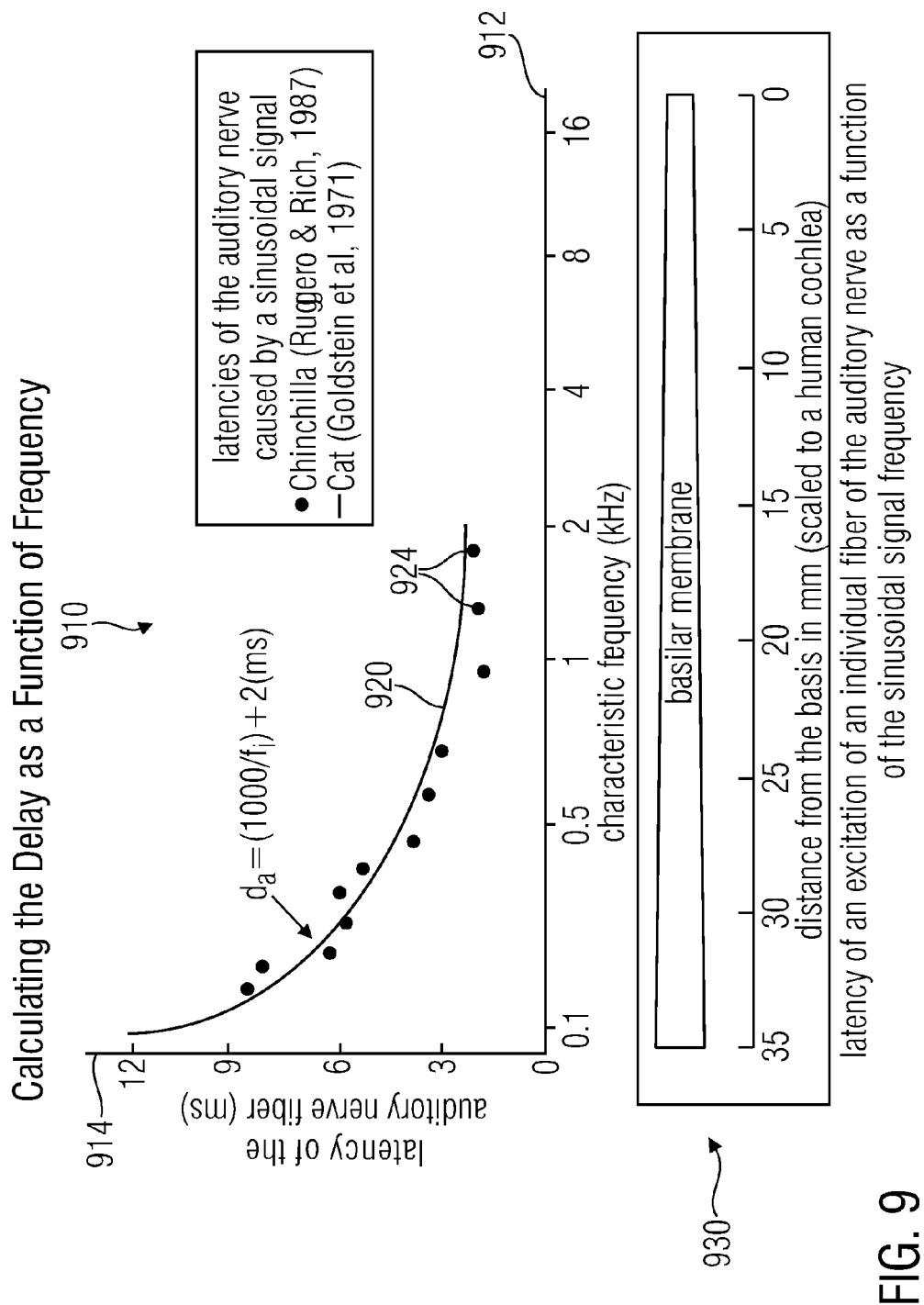
FIG. 9 shows a graphical illustration of a delay in a propagation of audio signals of difference frequencies on a basilar membrane.

For a further illustration, FIG. 9 shows a graphical representation of a delay in a propagation of signals of different frequencies on the basilar membrane. Here, a first graphical representation 910 describes a latency of auditory nerve fibers as a function of a characteristic frequency.

A frequency is here plotted at an abscissa 912 in a range between 0.1 kHz and 16 kHz. An ordinate of 914 describes a latency of the auditory nerve fiber in a range between 0 and 12 milliseconds. A curve 920 describes a course of a latency of the auditory nerve caused by a sinusoidal signal over the frequency for a cat. Measuring points 924 describe a similar course for a chinchilla. It was found that the latency on auditory nerve fibers as a function of a characteristic frequency $f_i$ for the respective nerve fiber may be described by the following equation:

$$d_a = (1000/f_i) + 2 ms.$$

The corresponding context is for example described in detail in the article "A Space-Time Theory of Pitch and Timbre Based on Cortical Expansion of the Cochlea Traveling Wave Delay" by S. Greenberg, D. Poeppel and T. Roberts, presented on the XIth International Symposium on Hearing, Grantham. For details reference is thus made to the corresponding article.

It is further noted here that a second graphical representation 930 shows a distance of auditory cells belonging to a characteristic frequency from a basis of a human cochlea. From this it may again be seen that auditory cells belonging to high frequencies are arranged close to the basis of the human cochlea, while auditory cells belonging to low frequencies are arranged remote from the basis of the human cochlea.

The present illustration consisting of the first graphical illustration 910 and the second graphical illustration 930 also shows, however, that a latency of the auditory nerve strongly increases for low frequencies (below approx. 0.5 kHz). From this it may be concluded that a propagation time close to the end of the basilar membrane (i.e. far from the basis of the cochlea) substantially decreases.

The described latency of the auditory nerve fibers results, as already described with reference to FIG. 8, in a curvature of trajectories in the neural activity pattern describing action potentials on a plurality of nerve fibers coupled to the auditory cells.

Figure 10:
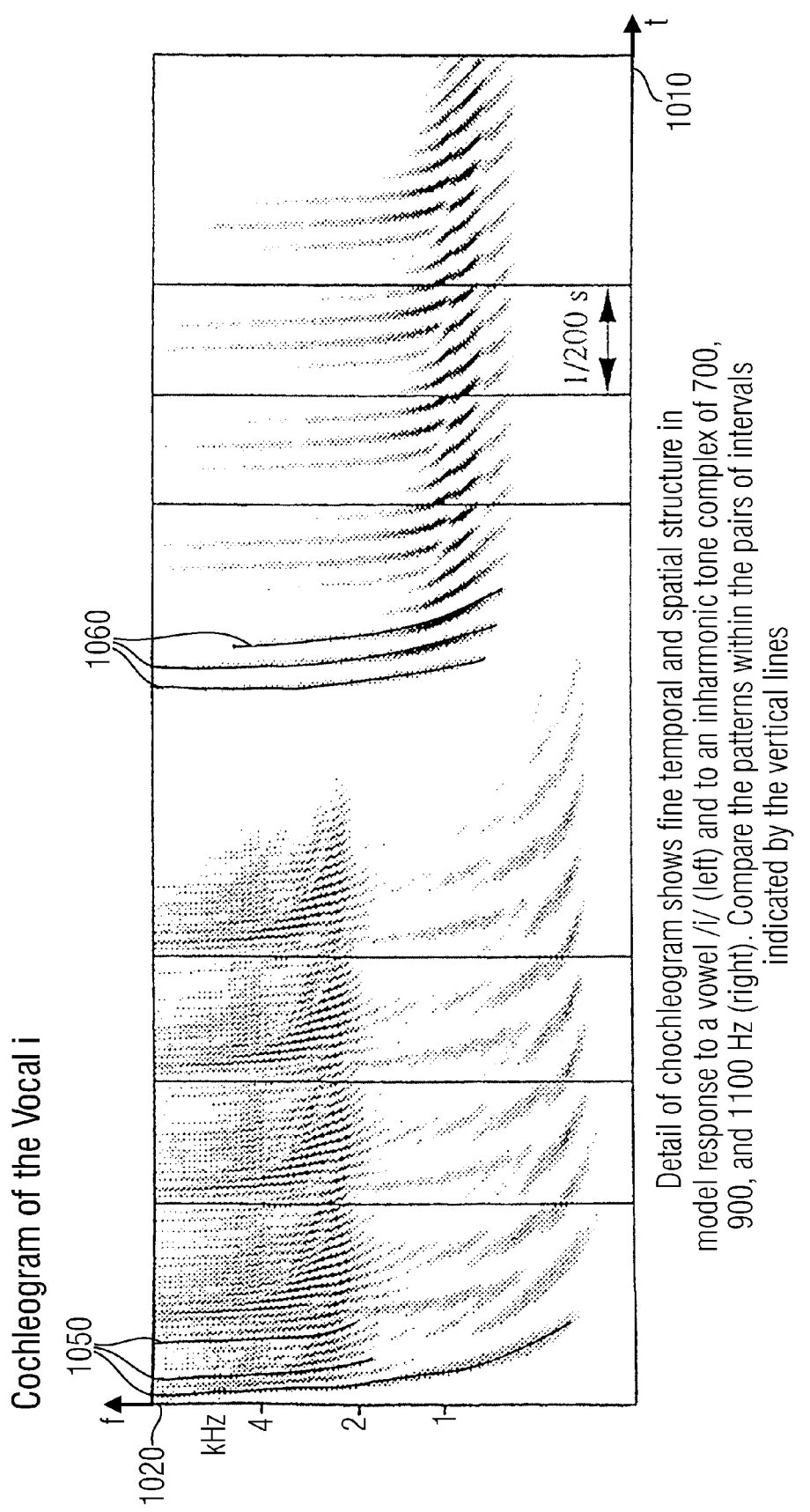
FIG. 10 shows a graphical illustration of a cochleogram for a vocal "i"

For a further illustration, FIG. 10 shows a graphical illustration of a cochleogram for a vocal "i" and for a non-harmonic tone complex of 700 Hz, 900 Hz and 1100 Hz. An abscissa 1010 here describes the time while an ordinate 1020 describes a frequency. In the corresponding cochleogram of the vocal "i" trajectories may again be clearly recognized, of which some selected trajectories are marked and designated by 1050. In a similar way, also the cochleogram of the non-harmonic sound complex shows trajectories designated by 1060.

Figure 11:
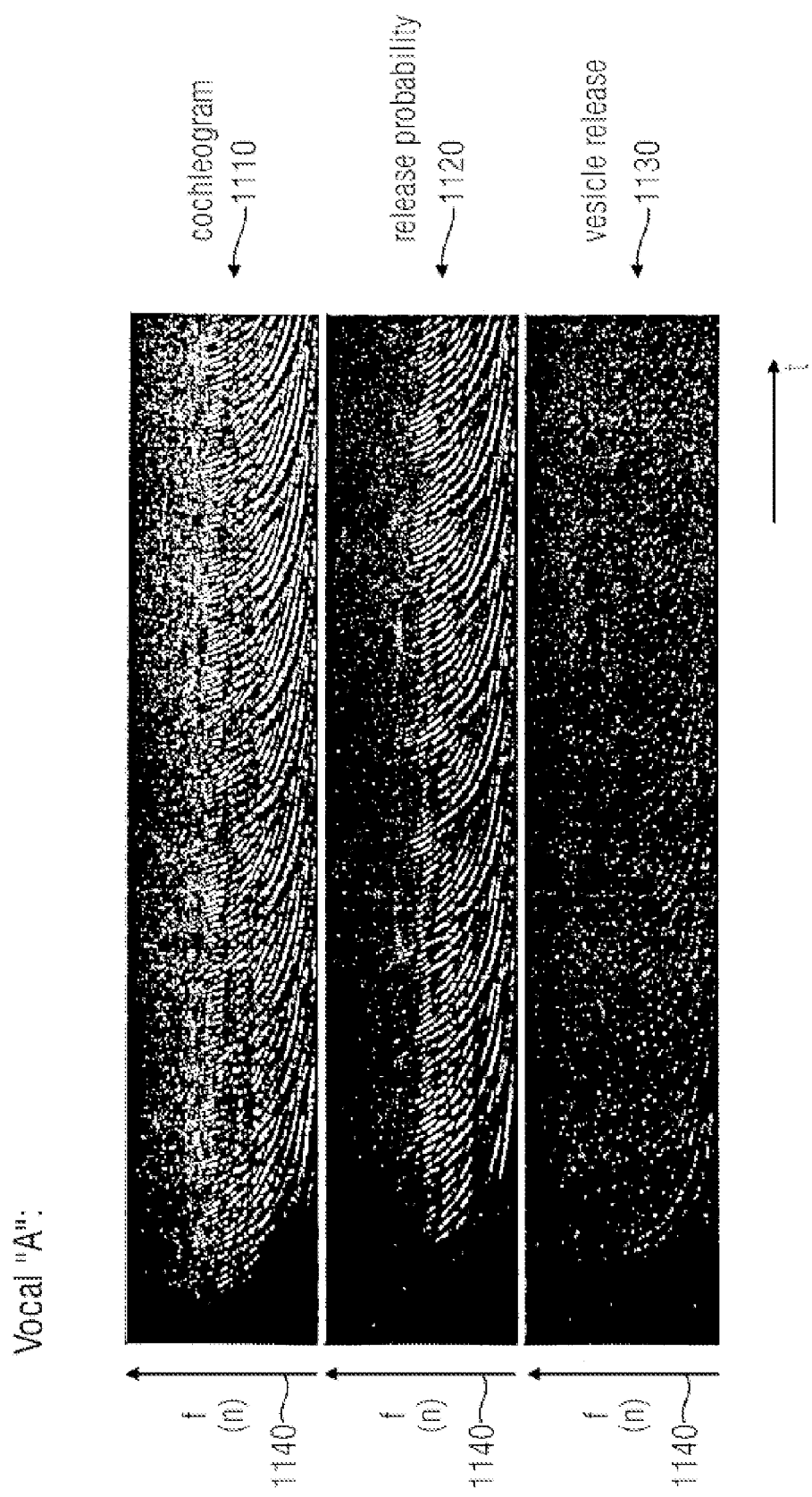
FIG. 11 shows a graphical illustration of a cochleogram, a transmitter release probability and a transmitter vesicle release for a vocal "A"

FIG. 11 shows a further graphical illustration of a cochleogram and a transmitter release probability and a transmitter vesicle release for a vocal "A". The cochleogram is here shown in a first graphical illustration 1110. A second graphical illustration 1120 describes a transmitter release probability based on the cochleogram. It is noted here that the cochleogram describes an excitation of the basilar membrane over time and frequency. Based on this, as described above, a release probability for neurotransmitter vesicles may be calculated by an analysis of the mechanical, chemical and electrical processes in an auditory cell. The release probability was for example designated as k(t). Based on the release probability k(t) then a neurotransmitter vesicle release may be calculated by a stochastic evaluation. An example for a resulting neurotransmitter vesicle release is shown in the third graphical illustration 1130. It may here be seen, that also the vesicle release over time and frequency comprises characteristic trajectories. These trajectories are then mapped by a modeling of the synaptic cleft onto trajectories of action potentials (i.e. trajectories in the neural activity pattern).

It is finally noted here that the frequency plotted at ordinates 1140 may respectively be associated with associated auditory cells or nerve fibers (n), respectively. Thus, the indicated trajectories occur in a very similar form also in the neural activity pattern.

Figure 12:
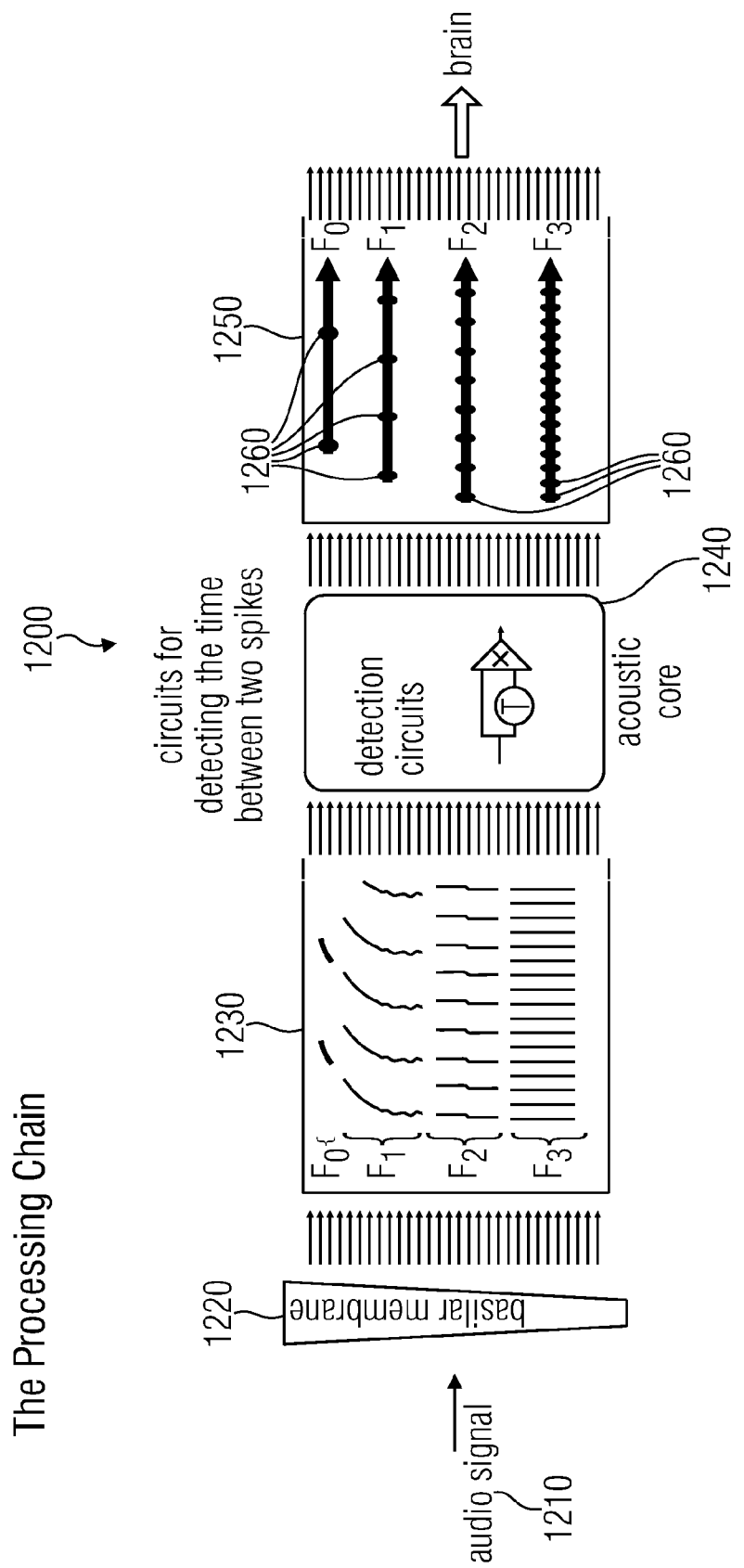
FIG. 12 shows a graphical illustration of a processing chain for an inventive analysis of an audio signal according to the second embodiment of the present invention.

FIG. 12 shows a graphical illustration of a processing chain for an inventive analysis of an audio signal according to the second embodiment of the present invention. The graphical illustration of FIG. 12 is in its entirety designated by 1200.

According to FIG. 12, based on an audio signal 1210 the movement of a basilar membrane 1220 is calculated at a plurality of locations (or positions or regions, respectively). An excitation pattern of the basilar membrane depending on a position along the basilar membrane is then either directly supplied to means for recognizing trajectories, or based on the excitation pattern of the basilar membrane a neural activity pattern is generated which is used for a further processing. The excitation pattern of the basilar membrane, just like a neural activity pattern derived from the same, comprises in an observation over time a plurality of trajectories which are characteristic for an audio signal. The trajectories are here typically curved, based on the run time differences between high and low frequencies described with reference to FIGS. 8 and 9. Apart from that it is to be noted, that the trajectories may for example also be interrupted. Further, in individual frequency ranges or spatial areas of the basilar membrane, respectively, different excitation patterns and trajectories may occur. Interrupted trajectories or partial trajectories, respectively, which are only excited in a certain frequency range, are for example characteristic for speech signals.

The indicated neural activity pattern 1230 or a basilar membrane excitation pattern, respectively, which is similar to the neural activity pattern, is then supplied to an acoustic core 1240. The acoustic core is implemented to detect a time between two peaks. Apart from that it is noted that it is the task of the acoustic core to identify trajectories in the neural activity pattern (or basilar membrane excitation pattern, respectively). The acoustic core may be implemented in order to analyze the complete frequency range, i.e. all nerve fibers forming the neural activity pattern, or only a selected partial range. It is further possible to analyze both different combinations of partial ranges and the complete frequency range in parallel.

The acoustic core 1240 is implemented in order to recognize a trajectory when a minimum number of regarded nerve fibers comprise an activity pattern 1230, which corresponds to a line-shaped course in the form of a typically curved line in a representation of nerve fiber number over time. The acoustic core 1240 then provides as an output signal a sequence of time information describing a temporal position of the trajectories. This may for example be the starting point in time of a trajectory or also a central point in time within a trajectory. Apart from that it is noted that it is of advantage to perform a parallel evaluation for a plurality of frequency bands or for a plurality of groups of nerve fibers, respectively, in order to make partial information available for a plurality of frequency bands for a further processing, e.g. a speech recognition. An exemplary output signal of an acoustic core 1240 is shown in the graphical illustration 1250. The output signal of the acoustic core 1240 here represents an improved analysis signal in which the amount of data with regard to the neural activity pattern 1230 is substantially decreased. The output signal 1250 of the acoustic core only describes discrete points in time for one or several frequency bands associated with trajectories. The discrete points in time are here designated by 1260. The information separated according to frequency bands describing the temporal position of trajectories are apart from that especially suitable for a speech recognition.

Figure 13:
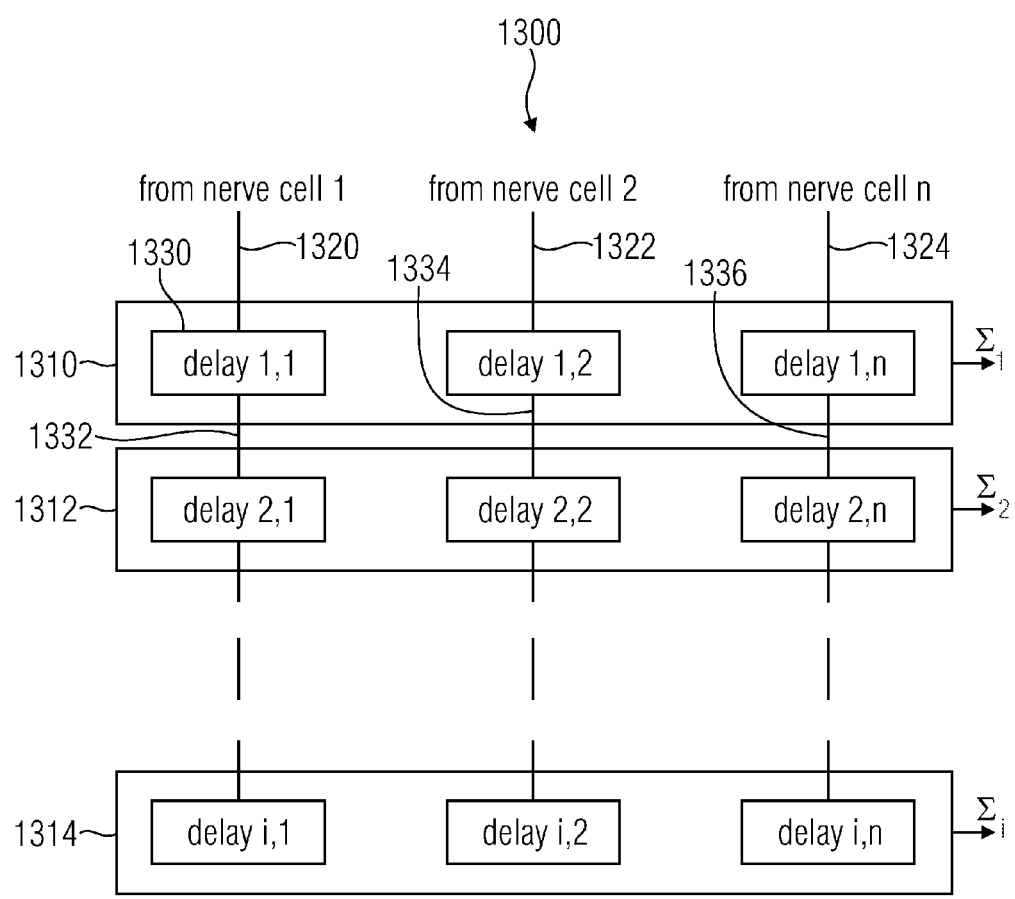
FIG. 13 shows a block diagram of a device for an inventive processing of the neural activity pattern according to the second embodiment of the present invention.

FIG. 13 shows a block diagram of a device for an inventive processing of the neural activity pattern. The device shown in FIG. 13 is designated by 1300 in its entirety. The indicated device 1300 comprises a plurality of stages 1310, 1312, 1314, wherein the first stage 1310 in parallel receives signals 1320, 1322, 1324 from nerve cells. The signals 1320, 1322, 1324 may describe action potentials on nerve fibers coupled to the corresponding nerve cells and thus describe the neural activity pattern.

In a first stage 1310 then for example the first nerve signal 1320 in a first delay means 1330 is subjected to a delay and advanced as a delayed nerve signal 1332 to a second stage 1312. In a similar way also the second nerve signal 1322 is delayed in the first stage 1310 and advanced as a delayed nerve signal to the second stage 1312. In the same way also the remaining nerve signals are processed in the first stage 1310 (i.e. for example also the $n^{th}$ nerve signal 1324).

The second stage 1312 is implemented in parallel to the first stage 1310, thus again enables the delayed advance of the delayed nerve signals 1332, 1334, 1336, whereby twice delayed nerve signals result. A device for an inventive processing of the neural activity pattern now includes a plurality of stages connected in series assembled like the first stage 1310 or the second stage 1312, respectively. The nerve signals 1320, 1322, 1324 are thus advanced in parallel through the plurality of stages 1310, 1312, 1314, wherein each stage adds a settable delay to the nerve signals.

Further, each of the stages 1310, 1312, 1314 is implemented to form a sum of the ingoing or outcoming nerve signals, respectively (or m times delayed nerve signals, respectively) at the same. Further, the stages 1310, 1312, 1314 may be implemented to compare this sum to a settable threshold value in order to determine whether at a given point in time at least a predetermined number of nerve signals or delayed nerve signals, respectively, (i.e. incoming nerve signals or outgoing nerve signals) are active (or comprise an action potential, respectively).

It is further of advantage that the delays of the delay means present in the stages 1310, 1312, 1314 are set differently, so that for example a first nerve signal 1320 when passing the stages 1310, 1312, 1314 is subjected to a different delay than the second nerve signal 1322. Delays may for example be set so that for the nerve signals 1320, 1322, 1324 different overall delays result when passing through the stages 1310, 1312, 1314 (wherein it is of course admissible that for example two nerve signals are delayed in the same way). In other words, means 1300 may be implemented so that not for all nerve signals the same delays result. It is apart from that advantageous that in the presence of j stages 1310, 1312, 1314 at least (j−1) stages 1310, 1312 are implemented so that the delay means contained in one stage do not comprise the same delay for the plurality of nerve signals. By this it may be achieved that a neural activity pattern incoming into an inventive means 1300 is distorted in time over time when passing through the described means, i.e. that individual nerve signals are shifted in time with regard to other nerve signals. By the distortion, in a time illustration curved line-shaped patterns, i.e. trajectories, may then be straightened in the neural activity pattern.

It is further noted that by the sum formation within a stage it may be seen when an originally curved trajectory was bent to be a straight line in the neural activity pattern (which is described by the fact that a given number of the delayed nerve signals comprise an action potential almost simultaneously or overlapping in time, respectively).

Figure 14:
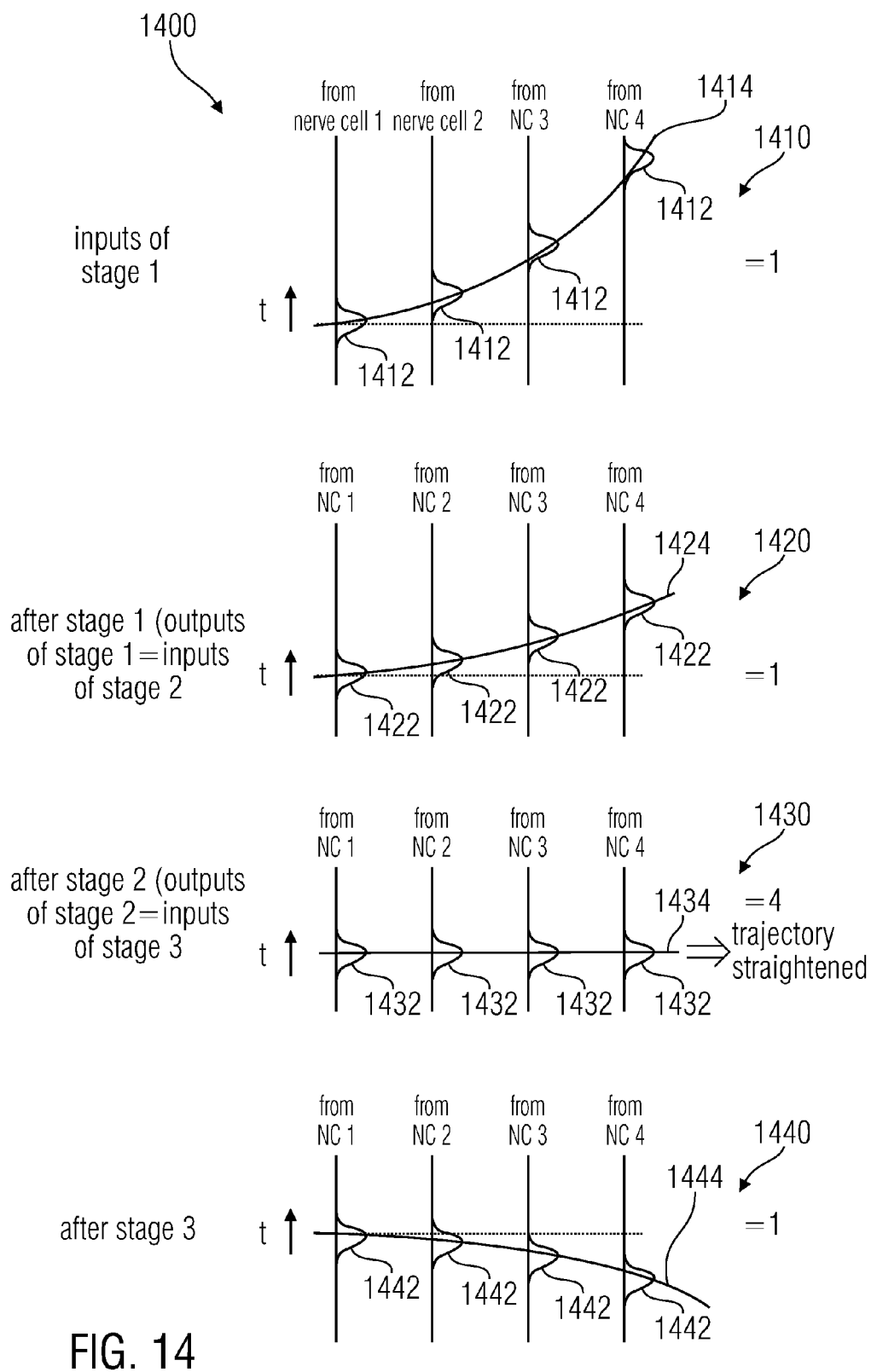
FIG. 14 shows a graphical illustration of signals in a device for an inventive processing of the neural activity pattern according to the second example of the present invention.

The functioning of means 1300 is to be illustrated with reference to FIG. 14. FIG. 14 shows an exemplary, graphical illustration of the signals in a device 1300 for an inventive processing of the neural activity pattern. The graphical illustration of FIG. 14 is in its entirety designated by 1400.

A first graphical illustration 1410 here describes an exemplary neural activity pattern at inputs of the device 1300. Here as an example the signals of four nerve cells (or on four nerve fibers, respectively) are shown as an example in a time course. Apart from that it is noted that the action potentials 1412 form a trajectory 1314. As it is shown, the trajectory 1414 in the temporal illustration comprises a strong curvature, as the action potentials 1412 of the different nerve fibers at the inputs of the first stage 1310 comprise a substantial offset in time. Thus, in the first stage 1310 at a fixed point in time respectively only one action potential is present, so that a threshold value for a sum of the action potentials applied to the first stage, which is for example set to be two, is not exceeded. Consequently, the first stage provides no output signal at a threshold value output.

A second graphical illustration 1420 describes the conditions at an output of the first stage 1310. It is here assumed that in the first stage 1310 the nerve signal provided from the first nerve cell NZ1 is delayed stronger than the nerve signals provided by the other stages. Apart from that it is assumed that in the given example the nerve signal provided from the fourth nerve cell NZ4 is delayed least, while the nerve signal from the third nerve cell NZ3 is delayed somewhat more and wherein the delays for the nerve signals from the nerve cells NZ2 and NZ1 increase more and more. In general, signals belonging to nerve cells responsive to a lower frequency are delayed less strong as compared to nerve signals from nerve cells detecting higher frequencies.

The second graphical illustration thus shows again action potentials 1424 as a function of time, wherein the action potentials 1422 form a trajectory 1424. As it may be seen from the second graphical illustration 1420, the curvature of the trajectory 1424 is less at the outputs of the first stage than a (time-place or time-frequency, respectively) curvature of the trajectory 1414 at the inputs of the first stage. This results from the different delays of the nerve signals associated with different nerve cells in the delay means (e.g. 1330) of the first stage. By this, a curved trajectory is so to speak straightened. As it may be seen from the second graphical illustration 1420, the second trajectory 1424 still comprises a residual curvature, however, so that the action potentials 1422 coming from different nerve cells or nerve fibers, respectively, are not all applied simultaneously to the outputs of the first stage 1310 or the inputs of the second stage 1312, respectively.

Also the second stage 1312 causes a further delay, wherein again signals of nerve cells sensitive with regard to low frequencies are delayed less than signals of nerve cells which are sensitive with regard to high frequencies. A third graphical illustration 1430 shows the nerve signals delayed again in the second stage 1312 at outputs of the second stage. It may be seen from the third graphical illustration 1430 that in the present example the nerve signals at the outputs of the second stage are respectively delayed so that action potentials 1432 of several nerve cells are simultaneously applied to the outputs of the second stage. In other words, a trajectory 1434 described by the action potentials 1432 is at least approximately straightened. The action potentials 1432 thus occur simultaneously or approximately simultaneously, respectively (at least overlapping in time, however), so that the simultaneous occurrence by a summation of the signals applied to the outputs of the second stage (or inputs of the third stage, respectively) comprises a distinct peak which is high enough in order to exceed a predetermined threshold value (e.g. two or three).

In other words, it may recognized by a suitable summing means (or another suitable means) when a curved trajectory was straightened. The corresponding information enables a conclusion back both to the starting point in time of the trajectory and also to the shape of the trajectory. It may be determined to be precise how many stages were passed before a trajectory was straightened. By this, when knowing the delays for the individual nerve signals in the stages of means 1300, also an original shape of the trajectory may be concluded. Further, the passage time for the stages may be known, so that also the point of time when a trajectory enters means 1300 may be determined. Thus, the analysis representation may include both characteristic time information of the trajectories and information about shape or curvature, respectively, of the trajectories.

The additional information about the shape of the trajectories may then be used advantageously in a further processing of the analysis representation, e.g. in order to facilitate a speech recognition or to improve a recognition quality in speech recognition.

Apart from that it is also noted that a fourth graphical illustration 1440 for improving the understanding also shows output signals at the outputs of a third stage. Action potentials 1442 describe a trajectory 1444 which is, however, again curved by a further bending of the trajectory.

It is noted that the delays in the stages 1310, 1312, 1314 may be achieved in different ways. The delay means (e.g. 1330) may for example be clocked and/or it may be continuously or discretely settable delay means. Apart from that it is also possible that one or several delay means are deactivated in a given stage for one or several nerve signals, so that several nerve signals are passed on through one stage with a delay as low as possible. Apart from that it is to be noted that means 1300 may all in all be implemented as an analog or digital circuit.

Figure 15:
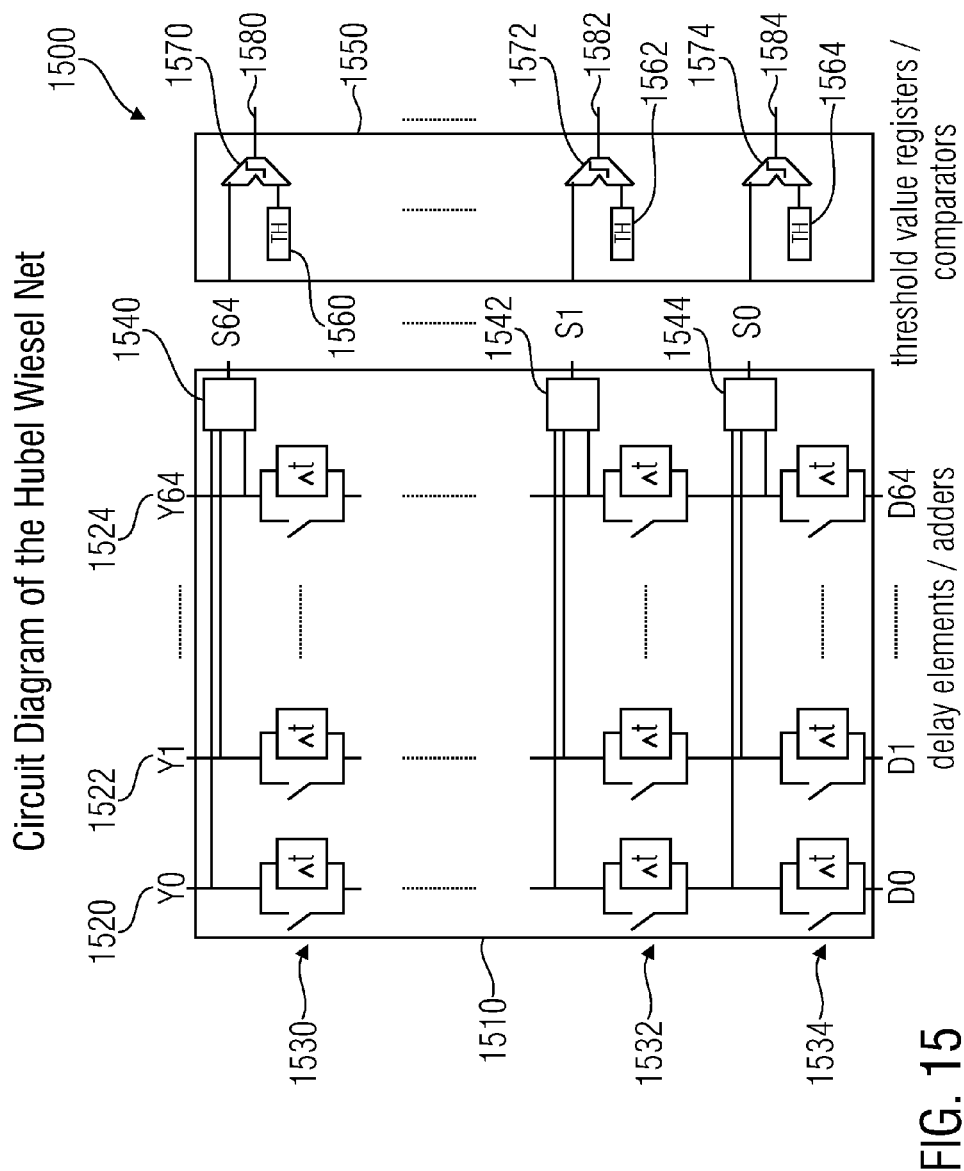
FIG. 15 shows a block diagram of a Hubel-Wiesel-network for an inventive calculation of an analysis representation of an audio signal according to the second embodiment of the present invention.

FIG. 15 shows a circuit diagram of an exemplary Hubel-Wiesel-network for an inventive calculation of an analysis representation of an audio signal according to the second embodiment of the present invention. The circuit diagram of FIG. 15 is in its entirety designated by 1500. A first circuit block 1510 receives input signals 1520, 1522, 1524, which may for example represent a neural activity pattern or an excitation pattern of a basilar membrane. The input signals 1520, 1522, 1524 are then passed through a plurality of stages 1530, 1532, 1534. An input signal 1520 thus passes through a plurality of stages 1530, 1532, 1534, wherein an input signal 1520 in one stage 1530, 1532, 1534 either passes through a delay means or is directly passed on to a subsequent stage. In other words, the delay means may also be bridged.

In other words, each stage includes, for each signal, a switchable delay means, wherein the delay means may be switched on or bridged in a signal path which an input signal runs through. Signals at the inputs of each stage are tapped and applied to summators 1540, 1542, 1544, wherein the signals respectively applied to the inputs of a stage are summed up. The first circuit block 1510 thus forms a grid of delay elements and adders connected in the indicated way.

The Hubel-Wiesel-network 1500 further comprises a threshold value means 1550, wherein one value each from a threshold value register 1560, 1562, 1564 and an output of a summator 1540, 1543, 1544 are supplied to a comparator 1570, 1572, 1574. Output signals 1580, 1582, 1584 of the comparator 1570, 1572, 1574 here provide an indication about whether at the inputs of a predetermined stage 1530, 1532, 1534 a number of signals is active simultaneously, wherein a minimum number at which an active output signal 1580, 1582, 1584 is output is determined by the threshold value registers 1560, 1562, 1564. In other words, by the comparators 1570, 1572, 1574 in connection with the summators 1540, 1542, 1544 and the threshold value registers 1560, 1562, 1564 it may be determined when (or after passing how many of the stages 1530, 1532, 1534) a trajectory is straightened which was read in via the inputs 1520, 1522, 1524 of the first block 1510.

The delays of the individual stages 1530, 1532, 1534 may here be given suitably in order to enable a recognition of a number of trajectories (or trajectory shapes, respectively) which is as large as possible.

Figure 16:
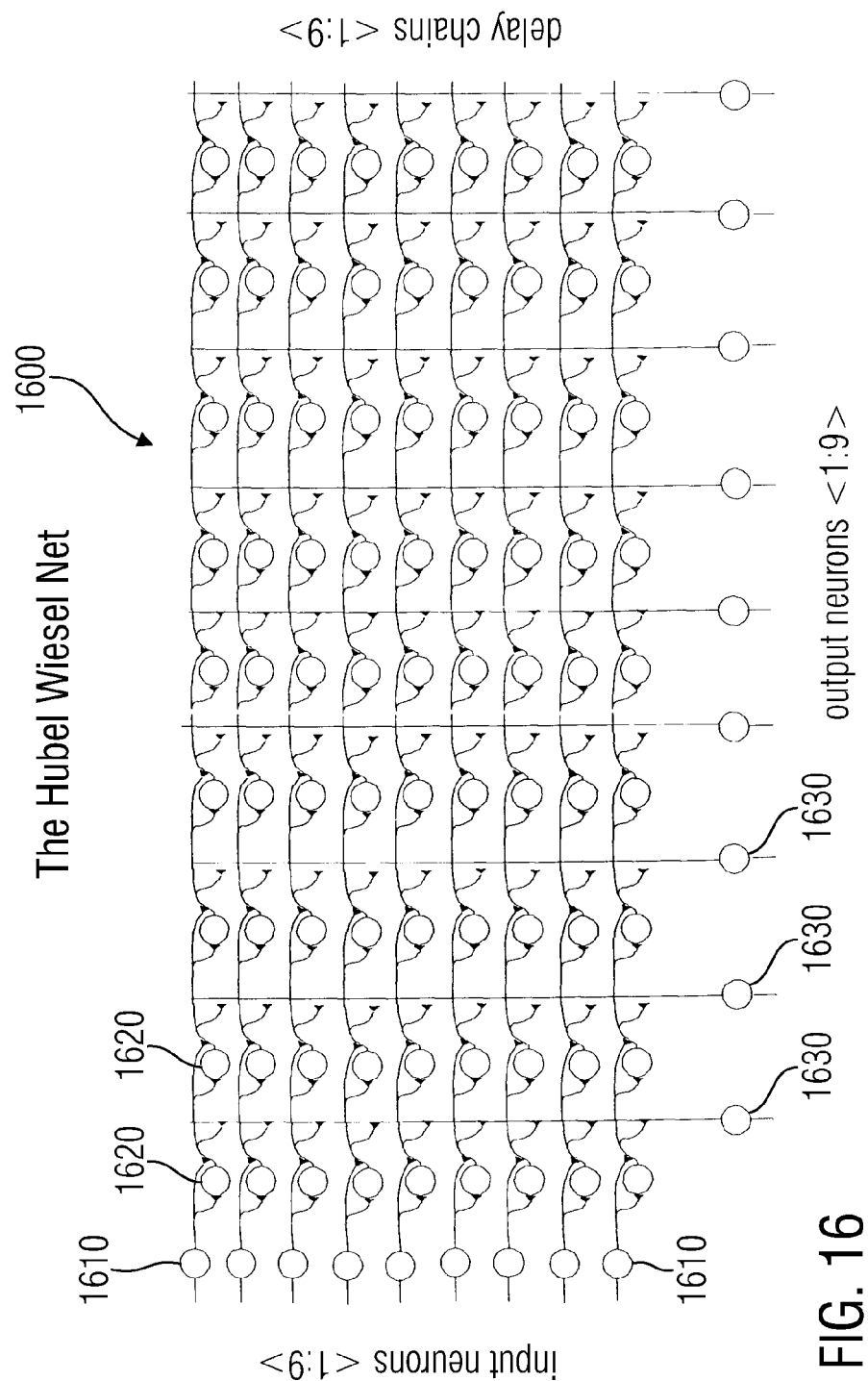
FIG. 16 shows a schematic diagram of a Hubel-Wiesel-network for an inventive calculation of an analysis representation of an audio signal according to the second embodiment of the present invention.

FIG. 16 shows a block diagram of a Hubel-Wiesel-network for an inventive calculation of an analysis representation of an audio signal according to the second embodiment of the present invention. The indicated Hubel-Wiesel-network is in its entirety designated by 1600.

Input neurons 1610 are laid out in order to receive a neural activity pattern or an excitation pattern of a basilar membrane of an ear model in the form of time signals provided in parallel. The neural activity pattern (or the excitation pattern of the basilar membrane, respectively) is here passed on with an optimum integration of delay neurons through several stages of the neural net. It is to be noted here that the delay neurons 1620 may also be bridged so that in a stage no delay of a signal provided from an input neuron 1610 takes place. The neural net further comprises output neurons 1630. The connection of the neural net 1600 may here be taken from FIG. 16. It is noted that the indicated neural net is able to recognize a curved curve or trajectory, respectively, in a neural activity pattern (or basilar membrane excitation pattern, respectively), input via the input neurons 1610 of the neural net 1600. The neural net is here (after a training) able to determine both point in time and also shape of a trajectory in a neural activity pattern input via the input neurons 1610, wherein an active output neuron describes this information. The information about the shape and time of a trajectory is hereby encoded by the fact, which output neuron is activated when.

Figure 17:
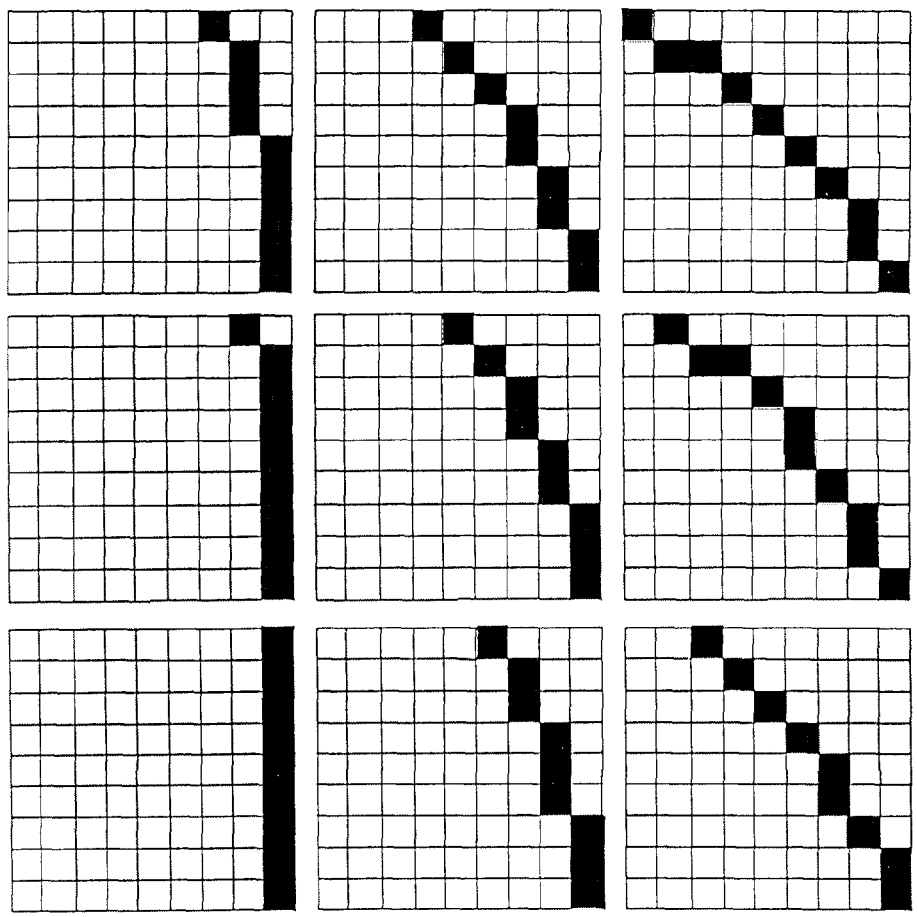
FIG. 17 shows a graphical representation of training patterns for training a Hubel-Wiesel-network.

FIG. 17 finally shows a graphical illustration of exemplary training patterns that may be used for training a neural net 1600. After a training the neural net 1600 is then able to identify correspondingly straight or curved courses as trajectories.

It may thus be noted, that a Hubel-Wiesel-network 1600 is very well suitable to recognize trajectories in a neural activity pattern. For this, the neural activity pattern is only to be applied to the inputs 1520, 1522, 1524 of the Hubel-Wiesel-network. At the outputs 1580, 1582, 1584 of the comparators 1570, 1572, 1574 then signals are available including an indication about shape and temporal position of a trajectory. The output signals 1580, 1582, 1584 may of course be brought in a form that is easier to interpret, as necessary, from which for example directly a time information about a trajectory may be seen. The time information then forms the advantageous analysis representation.

Apart from that it is noted, that the neural net 1700 designated in FIG. 17 which is very well suitable for a recognition of trajectories in a neural activity pattern is in detail described in the article "A neural net for 2 D-slope and sinusoidal shape detection" of A. Brückmann, S. Klefenz and A. Wünsche (published in the CIST International Scientific Journal of Computing, ISSN 1727-6209).

It is further noted that the processing of the neural activity pattern may be performed by the application of a so-called Hough transformation (see U.S. Pat. No. 3,069,654). A Hough transformation is able to recognize in an effective way successive trajectories in a space/time pattern. Thus, the Hough transformation is especially suitable for extracting an analysis representation from an audio signal, as within the scope of the present invention it has been found that trajectories in a neural activity pattern of an ear model represent characteristic information of the audio signal which may advantageously be used for a further analysis.

It is further noted that also other known methods may be used for a pattern recognition in order to recognize trajectories in the neural activity pattern. Here, especially advantageous such methods may be used that enable a recognition of curved lines, as it has been found, that trajectories in the neural activity pattern typically comprise a hyperbolic shape. It is to be considered here, that the neural activity pattern for a plurality of nerves over time results in a two-dimensional pattern, wherein along a first direction on several nerve fibers signals may be represented for example by an intensity distribution or by numerical values, respectively, whereas, however, in a second direction the temporal development is plotted. A typical way of illustration for a time course of a neural activity pattern may thus for example be similar to the indicated cochlea diagrams (cochleograms).

It is thus possible to employ any pattern recognition algorithm which is able to recognize curved lines. It has been found, however, that the application of a Hough transformation is in particular advantageous because the Hough transformation is especially suitable for a recognition of curved lines. Apart from that it is noted that when performing a Hough transformation in an arrangement 1600 or 1700, respectively, also when several closely neighbored trajectories are present, a good recognition result may be achieved, if only the threshold values or response sensitivities, respectively, of the output neurons (or the comparators, respectively) are suitably set.

It is further possible, within the scope of a Hough transformation (or another pattern recognition operation) to also recognize a length of a trajectory, so that apart from the information about point in time and shape of the trajectory still a third information for a subsequent analysis is available.

Apart from that it is noted that also a two-dimensional pattern comparison over the time illustration of the neural activity pattern may be performed in order to gain a sequence of time information describing a temporal position of consecutive trajectories.

It is further noted that it is advantageous to perform a pattern recognition based on an analysis representation of an audio signal. According to the present invention two especially advantageous analysis representations exist. It has been found, to be precise, that a neural activity pattern may especially advantageously be used for an analysis of an audio signal. Further, also a representation including time information about trajectories contained in the neural activity pattern is especially suitable for an analysis of the audio signal. Both the neural activity pattern and also the time representation including information about the trajectories contained in the neural activity pattern are in the following referred to as audio signal representatives.

Figure 18:
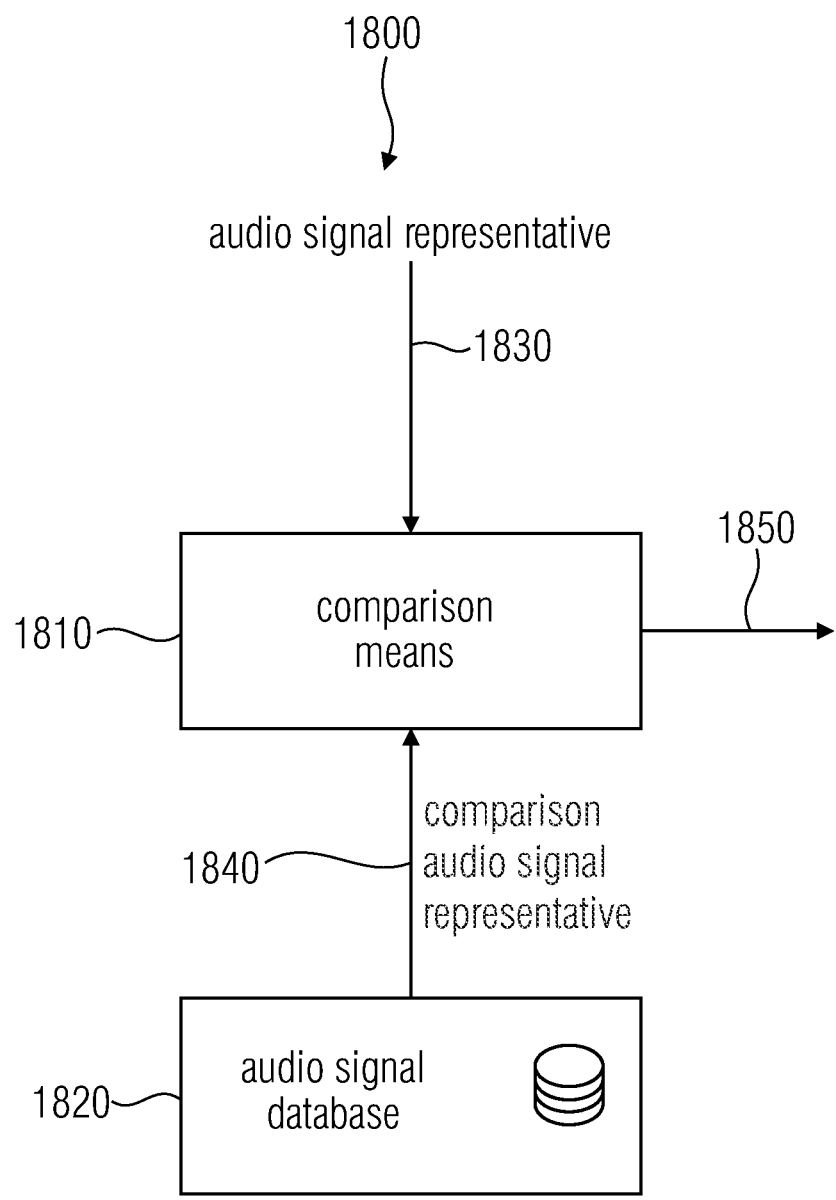
FIG. 18 is a schematical illustration of means for identifying an audio signal.

FIG. 18 shows a schematical illustration of means for identifying an audio signal. Means shown in FIG. 18 is in its entirety designated by 1800. The means includes a comparison means 1810 coupled to an audio signal database 1820. Comparison means 1810 is further supplied with an audio signal representative 1830. Based on the audio signal representative 1830 and the comparison audio signal representatives contained in the audio signal database, comparison means 1810 generates a comparison result 1850 including a statement about whether the audio signal representative 1830 comprises a similarity to at least one comparison audio signal representative 1840 stored in the audio signal database. The comparison result 1850 may of course also include a statement about the fact for which comparison audio signal representative 1840 the audio signal representative 1830 has the greatest similarity.

Comparison means 1810 may include any device for comparing two audio signal representatives. It is for example possible to use means which may determine a mathematic distance between the audio signal representative and the comparison audio signal representative based on mathematic methods. Further, a neural net may be used in order to compare the audio signal representative 1830 to the comparison audio signal representatives 1840. A neural net may for example respectively be trained with a plurality of audio signal representatives.

It is further noted that the audio signal database 1820 may for example include a plurality of comparison audio signal representatives describing pieces of music. It is further as well possible that the audio signal database includes comparison audio signal representatives which only describe individual tones, for example a vocal or a consonant. Thus, the indicated means 1800 for identifying an audio signal may also be used effectively for a speech recognition, wherein the selected audio signal representatives are especially suitable for such an application.

Figure 19:
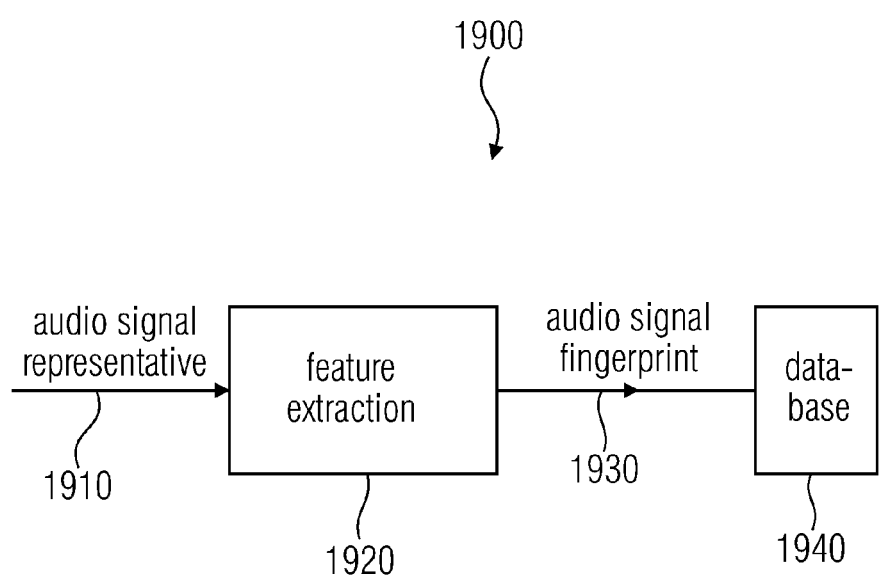
FIG. 19 is a schematical illustration of means for extracting an audio signal content.
Figure 20:
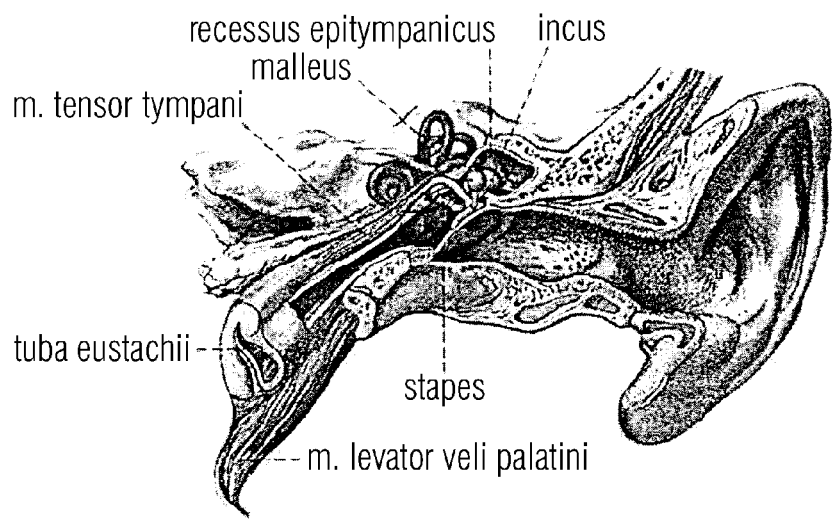
FIG. 20 is a graphical illustration of the auditory periphery.
Figure 21:
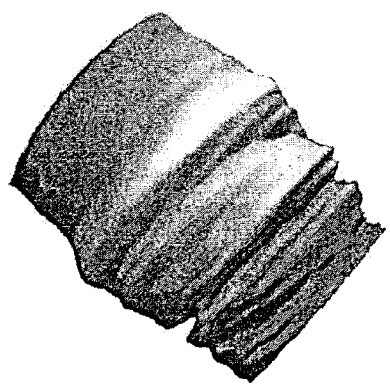
FIG. 21 is a graphical illustration of the outer ear transmission function.
Figure 22:
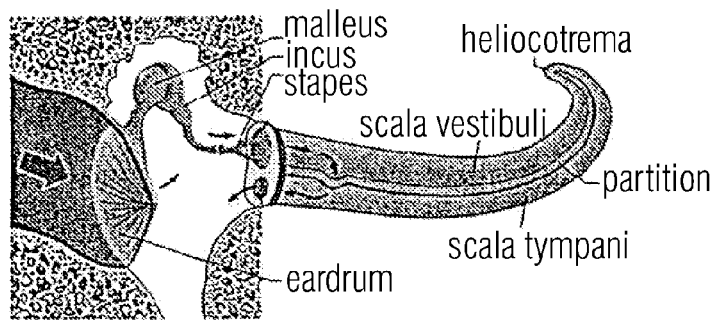
FIG. 22 is a graphical illustration of middle ear and rolled-out cochlea.
Figure 23:
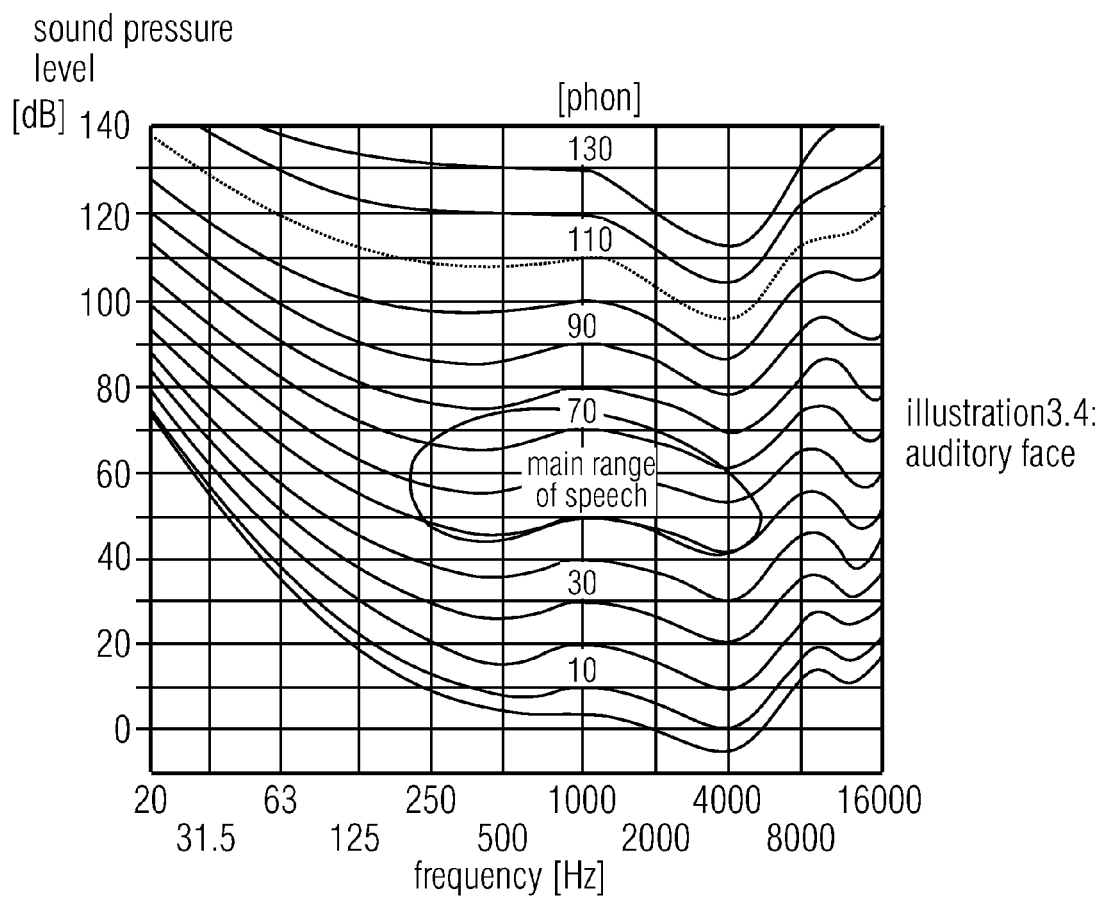
FIG. 23 is a graphical illustration of an auditory region.
Figure 24:
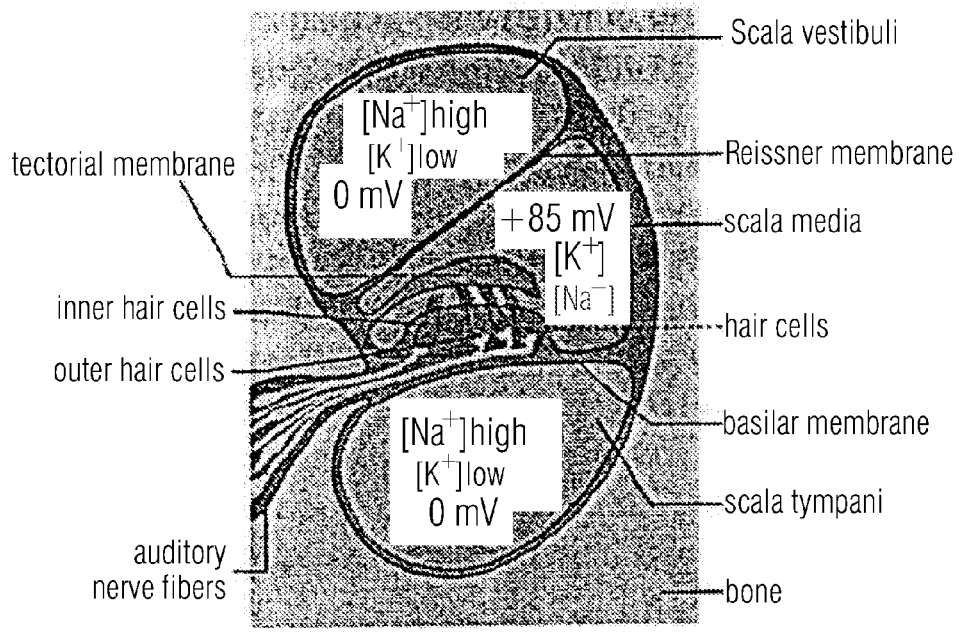
FIG. 24 is a graphical illustration of a section through a cochlea.
Figure 25:
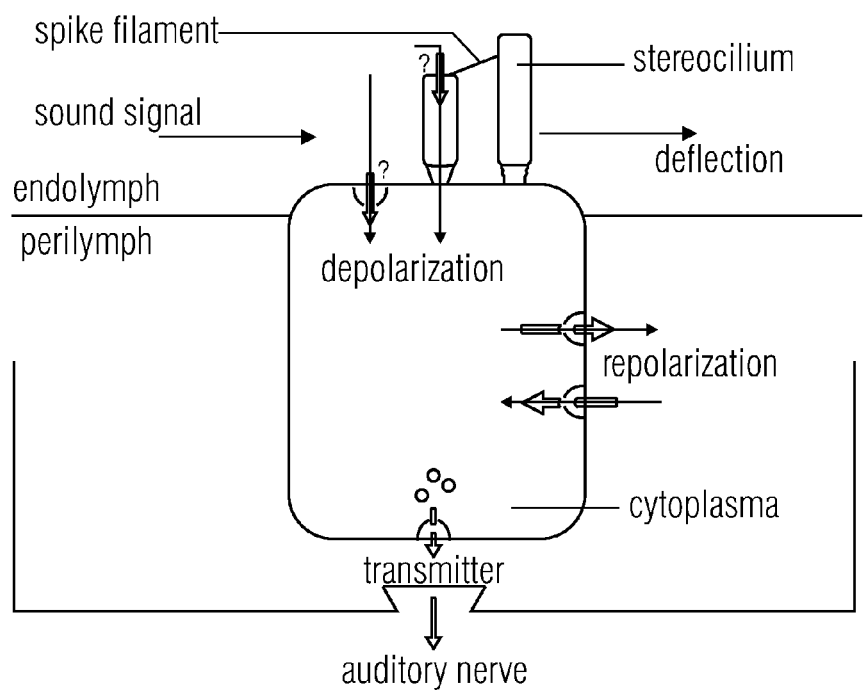
FIG. 25 is a schematical illustration of a hair cell.
Figure 26:
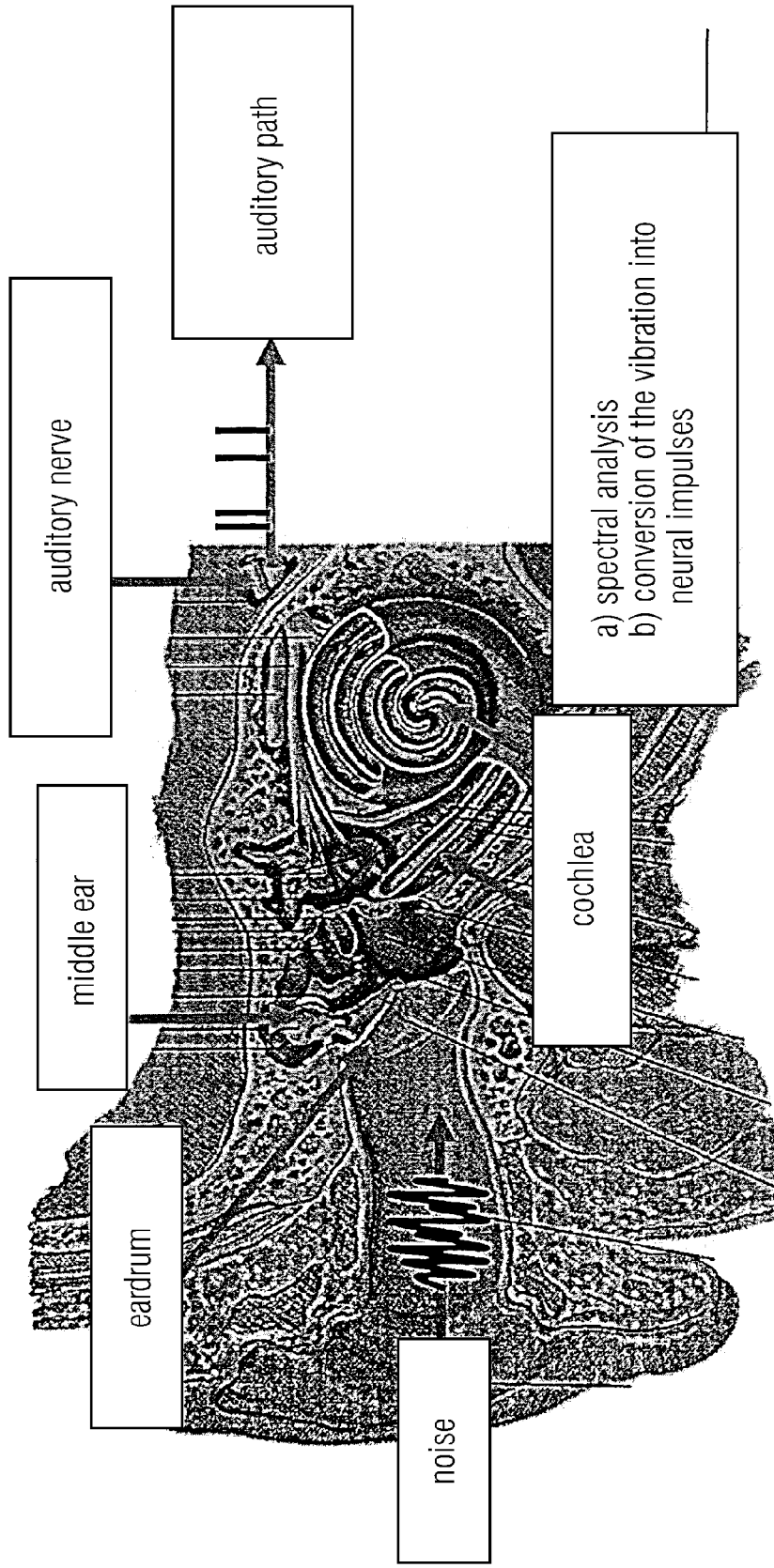
FIG. 26 is a graphical illustration of an anatomy of the auditory periphery.
Figure 27:
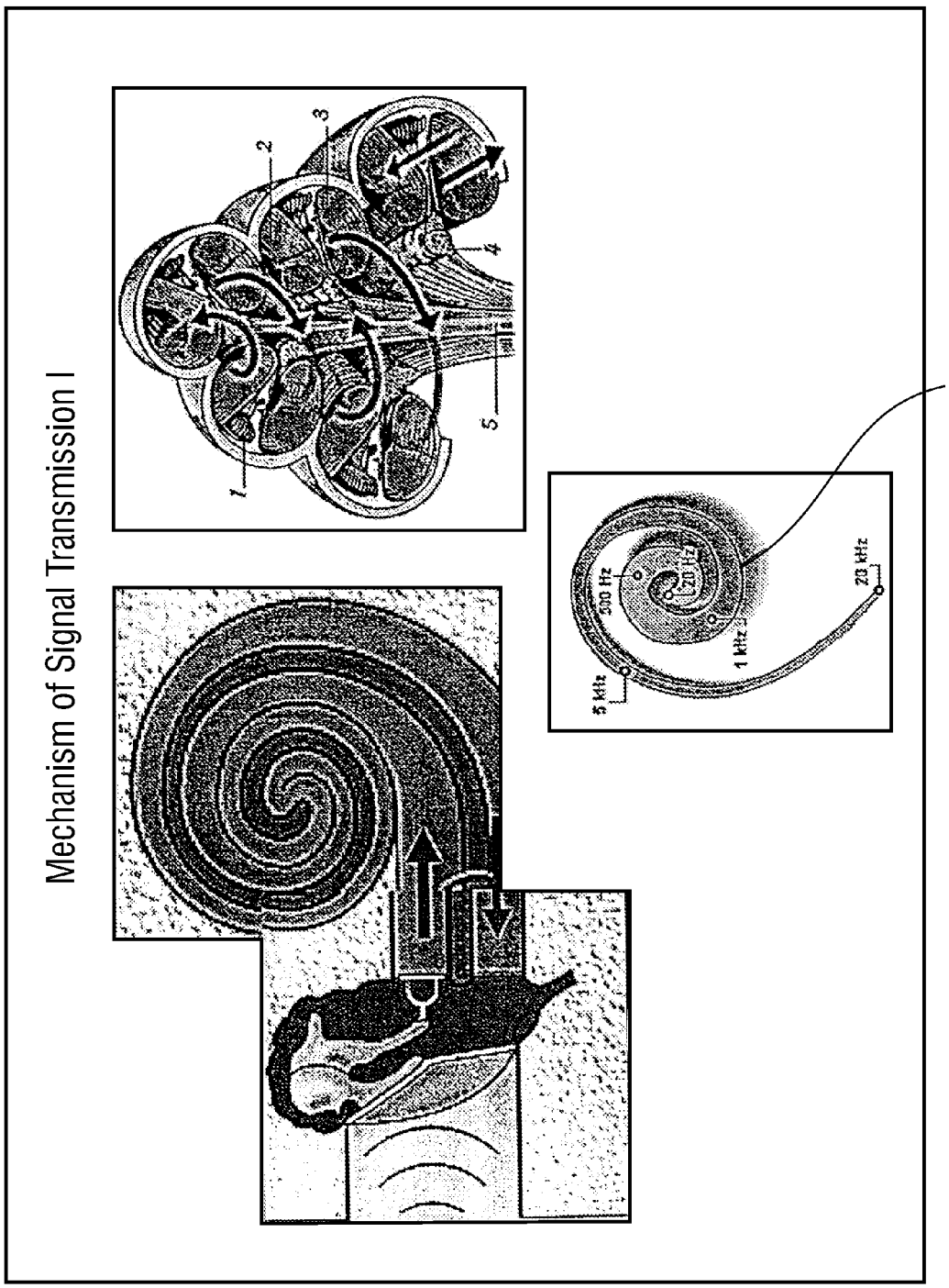
FIG. 27 is a graphical illustration of a mechanism of signal transmission in a human ear.
Figure 28:
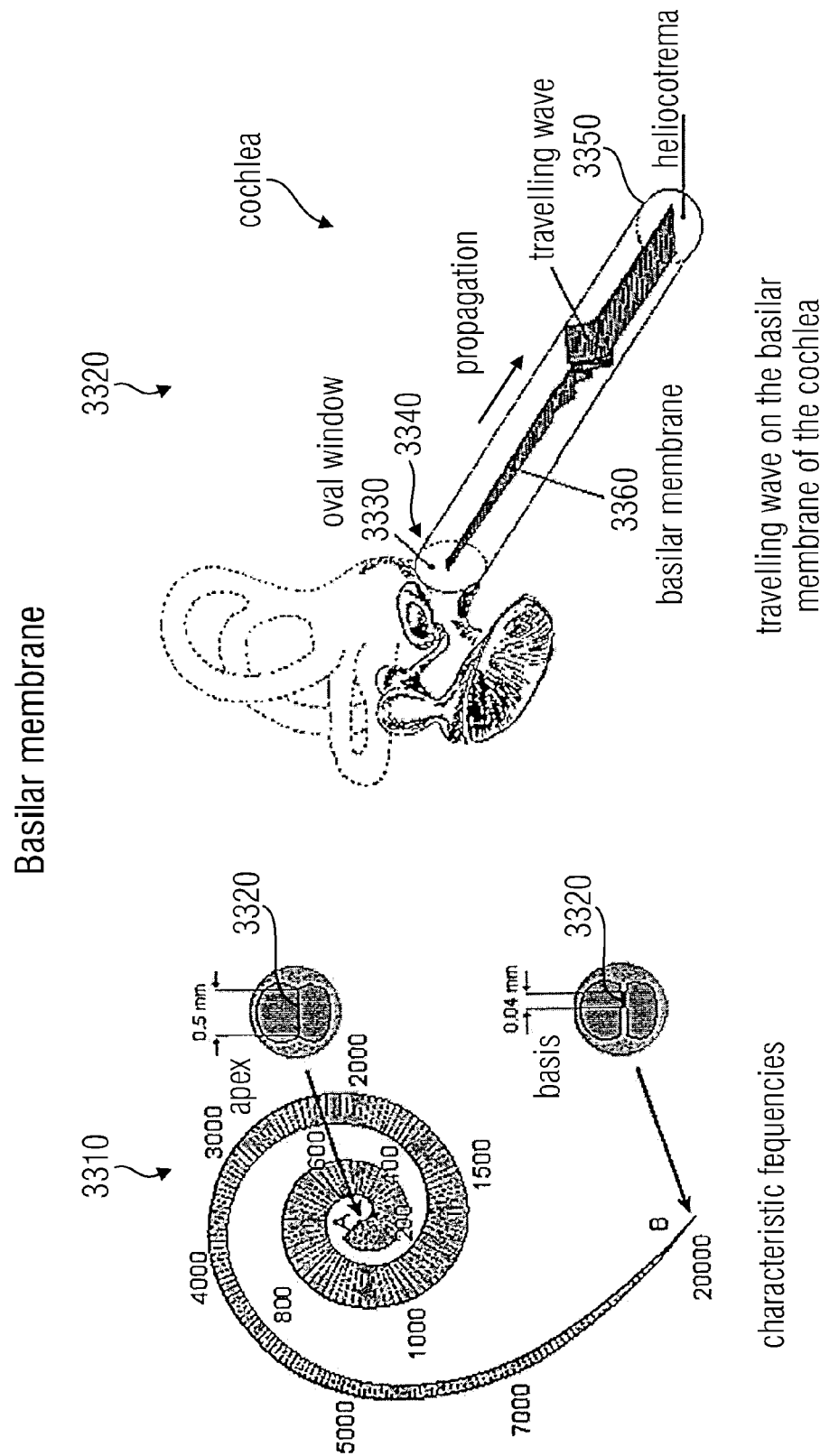
FIG. 28 is a graphical illustration of the geometry of the basilar membrane of a human ear and a reaction of the basilar membrane to an excitation.
Figure 29:
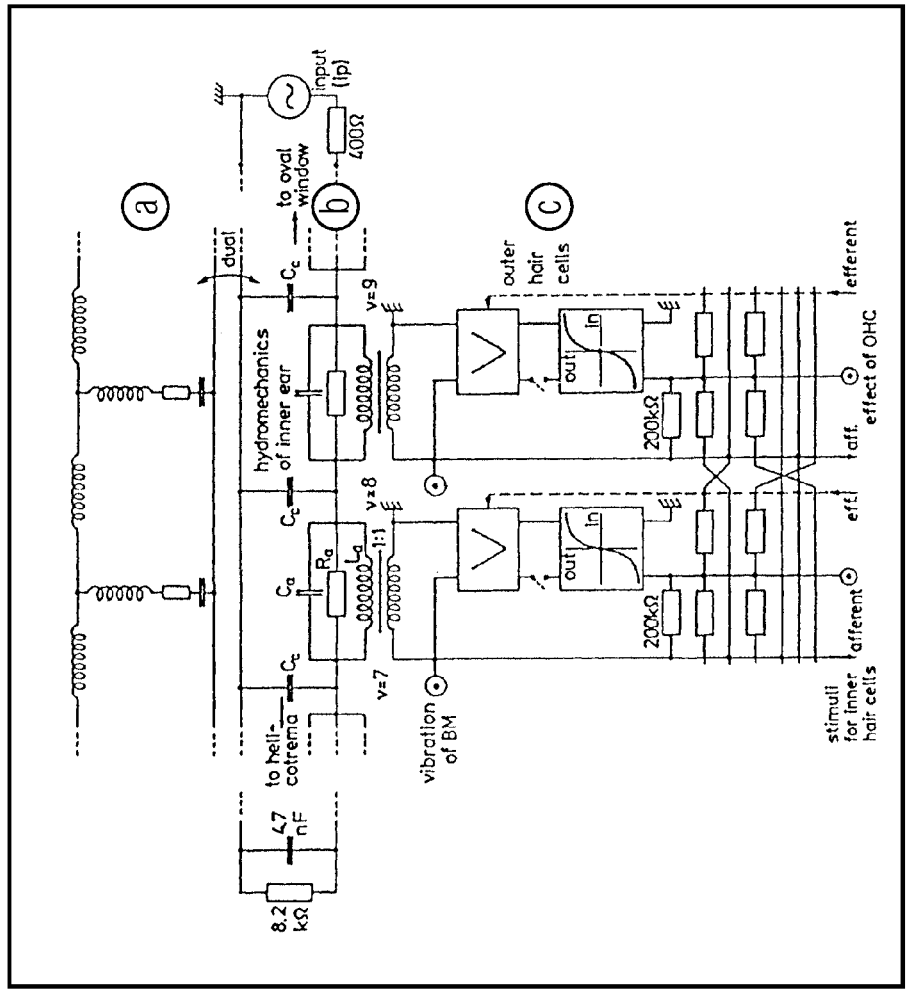
FIG. 29 is a graphical illustration of an extended Zwicker model for describing an inner ear.
Figure 30:
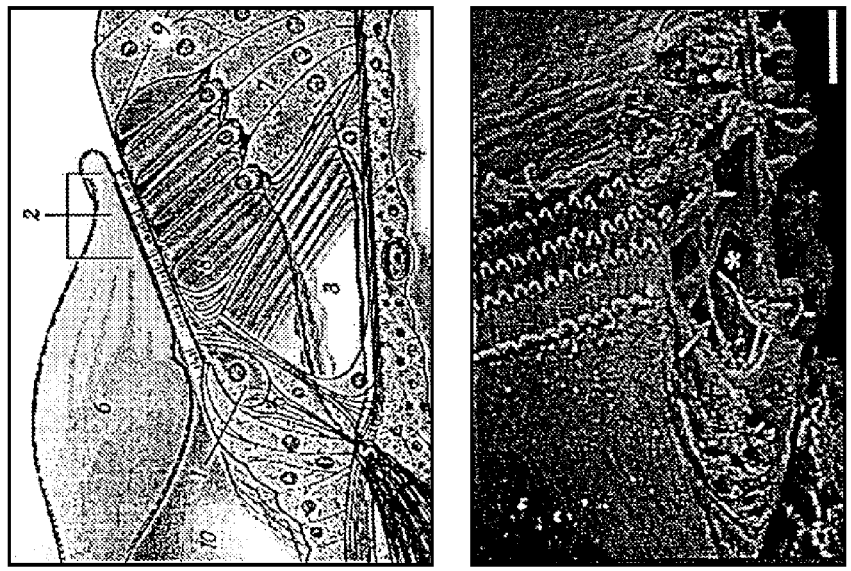
FIG. 30 is a graphical illustration of an organ of Corti.
Figure 31:
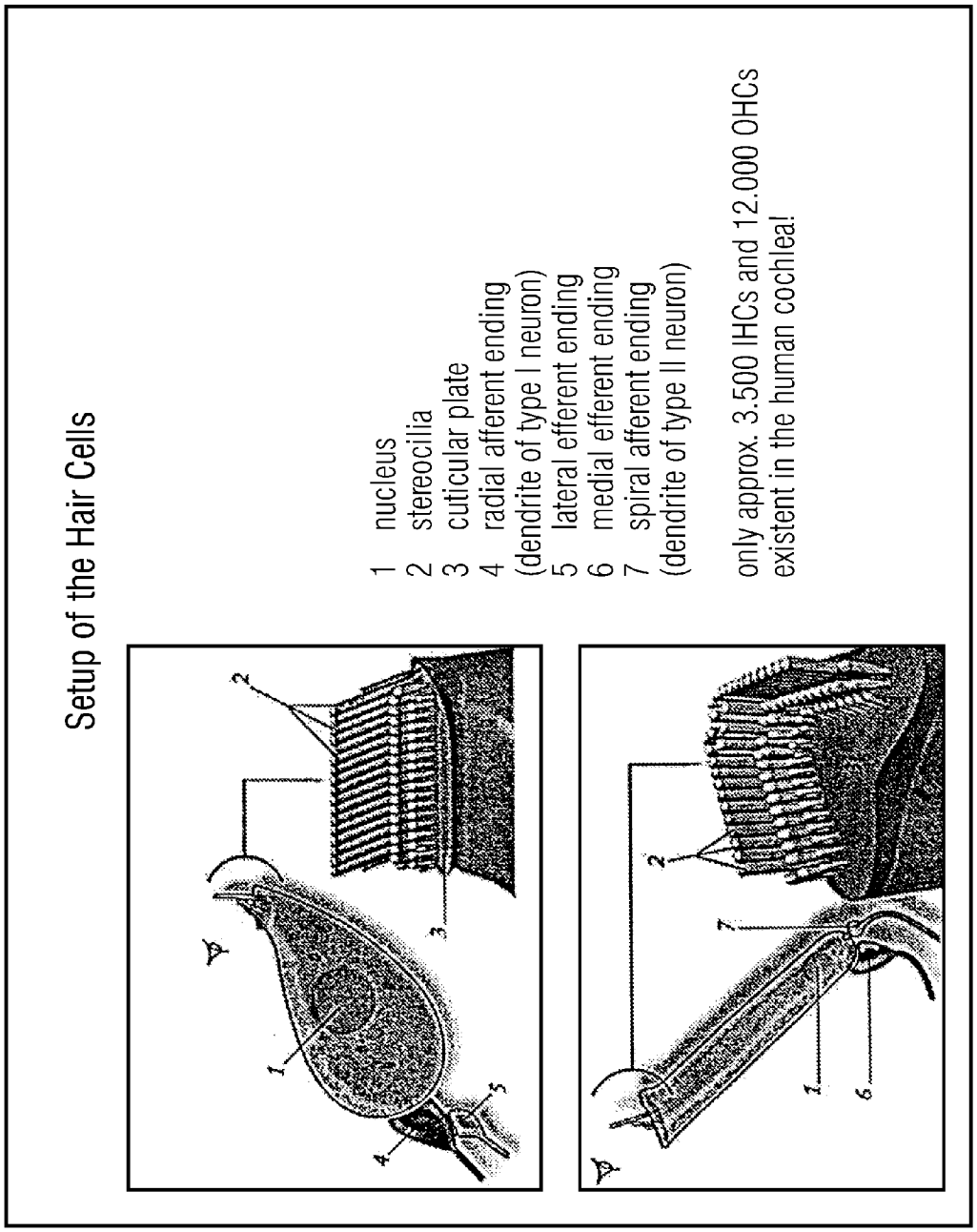
FIG. 31 is a graphical illustration of a setup of hair cells.
Figure 32:
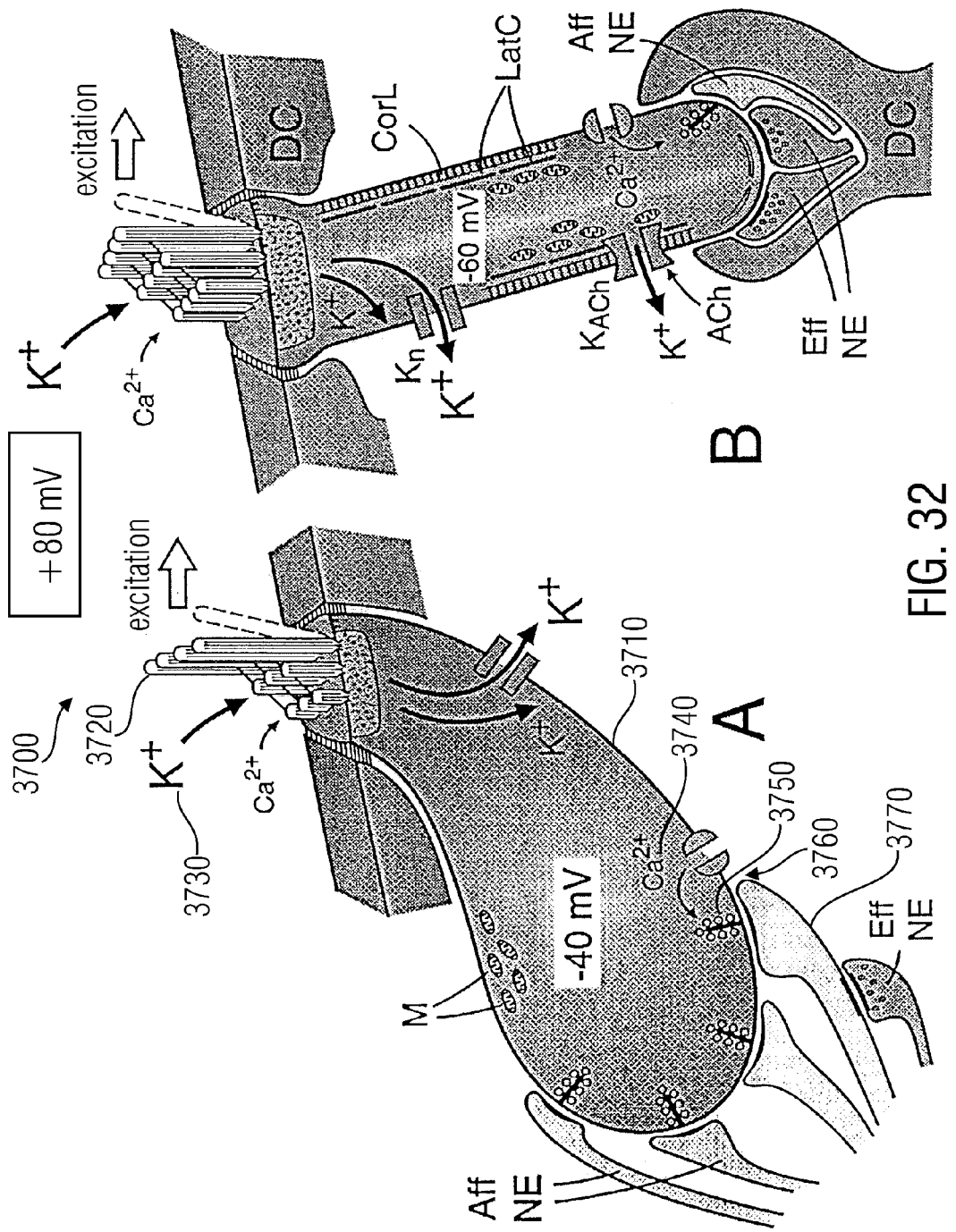
FIG. 32 is a graphical illustration of chemical processes in a hair cell.
Figure 33:
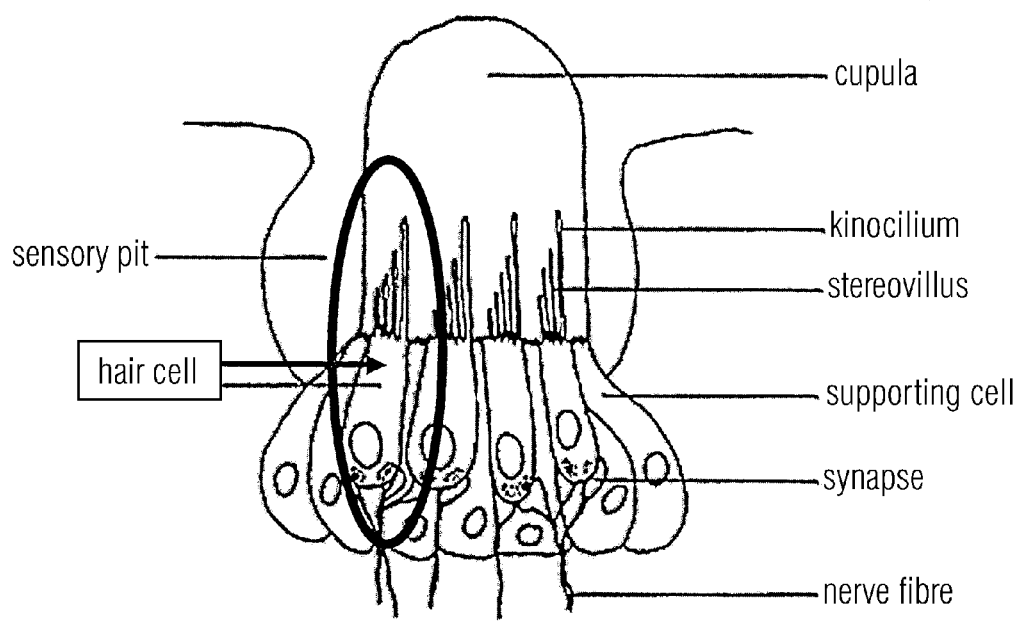
FIG. 33 is a graphical illustration of a sensory pit.

FIG. 19 shows a schematical illustration of means for extracting an audio signal fingerprint from the audio signal representative. Means shown in FIG. 19 for extracting the audio signal fingerprint is in its entirety designated by 1900. Here, an audio signal representative 1910 is supplied to means 1920 for feature extraction. Means 1920 for feature extraction generates, based on the audio signal representative 1910, an audio signal fingerprint 1930. The audio signal fingerprint 1930 may then be supplied to an audio signal database 1940.

Means 1920 for feature extraction may for example be implemented to extract a pitch and/or a rhythm from the audio signal representative 1910. If the audio signal representative is a neural activity pattern, then for example a pitch may be extracted by identifying those nerve fibers comprising a maximum activity in the neural activity pattern. The nerve fiber having the highest activity in the neural activity pattern is indeed a good measure for a pitch, as the nerve fibers typically comprise an advantageous frequency. Further, changes (or the corresponding points in time of the changes, respectively) may be used in the neural activity patterns in order to determine a rhythm of the audio signal. A recognition of changes in the neural activity pattern is possible comparatively simple, by forming a distance measure, e.g. a mathematical norm, between consecutive instantaneous values of the neural activity pattern. Significant changes may then be recognized when the distance measure exceeds a predetermined value.

Also methods for a pattern recognition may be applied to the audio signal representative 1910 in order to generate an audio signal fingerprint. The audio signal fingerprint may thus for example include combined information about a pitch and/or rhythm of the audio signal.

If the audio signal representative 1910 is further a representation including time information regarding trajectories contained in the neural activity pattern, then a feature extraction is possible in an especially simple way. For example time distances between the consecutive trajectories may be calculated which are then characteristic for the audio signal.

It has further been found, that a shape of the trajectories is an especially important feature. It is thus possible to only store information regarding trajectories of a special shape in an audio signal fingerprint, whereby an amount of data of the audio signal fingerprint 1930 may be reduced. This again enables an efficient storing of the audio signal fingerprint in a database.

It has further been found that several trajectories are typically associated with a sound event, comprising a characteristic shape and a characteristic distance. Thus, for example in the feature extraction 1920 a group of a plurality of trajectories may be evaluated, whereupon one symbol is respectively associated with a group of trajectories. A sequence of symbols belonging to consecutive groups of trajectories then form the audio signal fingerprint and may be stored in a database. Based on an analysis of a group of trajectories, further a speech recognition may be realized, as vocals and consonants respectively comprise characteristic trajectory patterns (regarding distance and shape of the trajectories) that may be recognized.

As a conclusion it may be said that the present invention provides a neural-physiological initialized model of the first stages of the auditory system. The model consists of a cochlea modeling, a harmonic oscillator model of the stereocilia movement equation and a model for a neurotransmitter vesicle release of the inner hair cells (IHC neurotransmitter vesicle release). Further, the inventive model includes a specification for the generation of post-synaptic action potentials. It is noted here that advantageously a spring stiffness constant value is used for the description of the stereocilia determined with the help of a raster force electron microscope. The inventive model may for example serve for optimizing a simulation of cochlea implants, as cochlea implants directly excite the auditory nerve.

It is a main advantage of the present invention that the device is adapted in a neuro-physiological way. Further, in an advantageous way a stochastic release of neurotransmitter vesicles is considered. For coupling the basilar membrane speed to the stereocilia movement, an inventive oscillator model is used, wherein the movement equation for the stereocilia movement is optimized. An equation of forces or an equation of movement, respectively, for the stereocilia movement is:

$$m\ddot{x} = -Dx - k\dot{x} + F_{ext} + F_{brown}.$$

Here, $Dx$ describes the spring return force, $k\dot{x}$ describes a laminar flow resistance, $F_{ext}$ (proportionality constant x basilar membrane speed v) describes an excitement and $F_{brown}$ describes a stochastic thermal force by an impact movement of the atoms.

A post-synaptic generation of action potentials is modeled in the same way (see E. Neher and T. Sakaba: "Quantal release parameters estimated from noise" J. Neuroscience, Dec. 15, 2001, 21 (24):9638-9654).

In other words, the present invention shows a device for an analysis of an audio signal, wherein the first stages of the auditory system from the mechanical conversion of sound in the inner ear, the transmission through the ossicles, the hydromechanic oscillation excitation of the cochlea, the mechano-electrical conversion at the inner hair cells up to the generation of the pulse spikes of the spiral ganglia cells of the auditory nerve are modeled.

A special advantage of the present invention is the use of the model employed for a basilar excitation. Further, in the present invention an especially advantageous modeling of the inner hair cells is used. A release of neurotransmitters in a synaptic cleft according to the present invention takes places packed in vesicles. The present invention further includes an especially advantageous model of a coupling between the basilar membrane and a movement of the stereocilia, wherein a harmonic oscillator model was used. A further advantage of the present invention lies also in a neuro-physiological initialization. For a spring stiffness constant an IHC table value was assumed for the mouse. A post-synaptic spike generation takes place according to the invention using a diffusion/refractory model. The present invention is thus able to very realistically reproduce auditory processes, i.e. generate and analyze the same.

Apart from that it is to be noted that the present invention also provides a device for the expansion of cochlea traveling waves. The corresponding device is based on a frequency-dependent calculation formula for delay trajectories along a basilar membrane. The formula is based on the works of Greenberg. The delay of the trajectories results through the wave group speed in a propagation of an impulse on the basilar membrane of an ear model. Low frequencies result in a time-delayed response on the basilar membrane, as the low frequencies are registered at the end of the basilar membrane. Thus, for the low frequencies the run time delay of the basilar membrane is effective.

Curved traces or trajectories, respectively, may advantageously be determined using a Hough transformation. Thus, the Hough transformation is very suitable to recognize circles, ellipses or lines but also other line-shaped curves may be recognized using a Hough transformation. Apart from that it is noted that a timing feed forward network according to the Hubel-Wiesel theory may itself learn patterns like bars or sinusoidal audio signals of a different frequency. In other words, a Hubel-Wiesel-network may learn a Hough transformation in a self-structuring and self-organizing way according to a described delay line method.

A special finding of the present invention is that the Hough transformation is directly coupled to the auditory nerve of an ear model for gaining information from the parallel pulse spiking trains. In other words, the Hough transformation is directly flanged to the auditory nerves in order to process the parallel pulse spiking trains. The Hough transformation here straightens delayed trajectories and detects both the signal shape (curvature) and also the occurrence point in time of the trajectories. In the Hough transformation, the data continuously pass through several stages. A time windowing is here not necessary, in contrast to other analysis methods.

In other words, the present invention models the first stages of the auditory system, from the mechanical sound conversion in the inner ear, the transmission through the ossicles, the hydromechanical oscillation excitation of the cochlea, the mechano-electrical conversion at the inner hair cells up to the generation of pulse spikes in the spiral ganglia cells of the auditory nerve. Every audio signal generates a two-dimensional basilar membrane speed profile plotted over time, wherein the basilar membrane may be separated into n sections. A click impulse here generates a traveling wave movement on the basilar membrane. A delay trajectory of the fiber latency of the auditory nerve (AN fiber latency) of a sinusoidal excitation signal is frequency-dependent and is calculated according to the formula of Greenberg $d_a = 1000/f_t + 2$ ms. An audio signal for example including vocals is given by a bundle of delay trajectories, wherein the delay trajectories comprise a respectively frequency-dependent form.

The present invention hereby enables to detect the delay trajectories. Here, an inventive Hubel-Wiesel neuro-simulator may be used that may itself learn the detection of sinusoidal patterns or straight lines. A corresponding Hubel-Wiesel neuro-simulator may learn a parallel Hough transformation which may advantageously be used in an inventive device for generating an analysis signal based on an audio signal.

The delay trajectories are in an inventive way determined by a parallel Hough transformation, wherein it is indicated at which point in time which delay trajectory is recognized in order to identify the present signal shape by this. In an inventive use of a Hough transformation from a neural activity pattern directly a size-shape-image may be generated in one step. A further analysis of the audio signal may in an inventive way take place in a Hough-space.

It is further noted that the inventive device also defines an inventive method. The method may be performed in any way, wherein an electronic calculating means is especially suitable for performing the inventive method.

In other words, the inventive device and the inventive method may be implemented in hardware or in software. The implementation may take place on a digital storage medium, for example a floppy disc, a CD, a DVD or a flash memory having electronically readable control signals that may cooperate with a programmable computer system so that the corresponding method is performed. In general, the present invention thus also consists in a computer program product having a program code stored on a machine-readable carrier for performing the inventive method when the computer program product runs on a computer. In other words, the invention may thus be realized as a computer program having a program code for performing the method, when the computer program runs on a computer.

The present invention thus shows the processing of a basilar membrane oscillation pattern with the help of the Hough transformation.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations, and equivalents as fall within the true spirit and scope of the present invention.

The invention claimed is:

1. A device for analyzing an audio signal to acquire an analysis representation of the audio signal, comprising:
   a converter for converting the audio signal into a representation representing a neurotransmitter vesicle occurrence in clefts between a plurality of nerve fibers and inner auditory cells of an ear model;
   a calculator for calculating a neural activity pattern over time on the plurality of nerve fibers resulting based on the neurotransmitter vesicle occurrence, wherein the neural activity pattern is the analysis representation of the audio signal;
   a coupler arranged to output the neural activity pattern to a plurality of nerve fibers of a human patient as electrical and/or chemical excitations; wherein
   the converter for converting the audio signal includes:
      a converter for converting the audio signal into a representation describing a movement of a basilar membrane in the ear model;
      a converter for converting the representation describing the movement of a basilar membrane into a representation describing a deflection of a stereocilium of a hair cell coupled to the basilar membrane; and
      a converter for converting the representation describing the deflection of the stereocilium into a representation describing the neurotransmitter vesicle occurrence;
   the converter for converting the representation describing the movement of the basilar membrane into the representation describing the deflection of a stereocilium is implemented to describe the stereocilium by a model of a harmonic oscillator which comprises a spring return force and an attenuation based on a laminar flow resistance;
   the model of the harmonic oscillator is implemented so that an excitation of the harmonic oscillator takes place by a second force component $F_{stoch}$ which describes a stochastic thermal force; and
   the device for analyzing the audio signal comprises a hardware implementation, or the device for analyzing the audio signal is implemented using a computer.

2. A device for analyzing an audio signal to acquire an analysis representation of the audio signal, comprising:
   a converter for converting the audio signal into a representation representing a neurotransmitter vesicle occurrence in clefts between a plurality of nerve fibers and inner auditory cells of an ear model;
   a calculator for calculating a neural activity pattern over time on the plurality of nerve fibers resulting based on the neurotransmitter vesicle occurrence, wherein the neural activity pattern is the analysis representation of the audio signal;
   a coupler arranged to output the neural activity pattern to a plurality of nerve fibers of a human patient as electrical and/or chemical excitations; wherein
   the converter for converting the audio signal includes:
      a converter for converting the audio signal into a representation describing a movement of a basilar membrane in the ear model;
      a converter for converting the representation describing the movement of a basilar membrane into a representation describing a deflection of a stereocilium of a hair cell coupled to the basilar membrane; and
      a converter for converting the representation describing the deflection of the stereocilium into a representation describing the neurotransmitter vesicle occurrence;
   the converter for converting the representation describing the movement of the basilar membrane into the representation describing the deflection of a stereocilium is implemented to describe the stereocilium by a model of a harmonic oscillator which comprises a spring return force and an attenuation based on a laminar flow resistance;
   the model of the harmonic oscillator is described by a movement equation of the following form:

$$m\ddot{x} = -Dx - K\dot{x} + F_{ext}(t) + F_{stoch}(t)$$

wherein $-Dx$ represents a spring return force;
   wherein $-K\dot{z}$ represents a laminar flow resistance;
   wherein $F_{ext}$ represents an external force, which is proportional to a velocity $v(t)$ of the basilar membrane; and
   wherein $F_{stoch}$ represents a stochastic thermal force by an impact movement of atoms; and
   the device for analyzing the audio signal comprises a hardware implementation, or the device for analyzing the audio signal is implemented using a computer.

3. A device for analyzing an audio signal to acquire an analysis representation of the audio signal, comprising:
   a converter for converting the audio signal into a representation representing a neurotransmitter vesicle occurrence in clefts between a plurality of nerve fibers and inner auditory cells of an ear model;
   a calculator for calculating a neural activity pattern over time on the plurality of nerve fibers resulting based on the neurotransmitter vesicle occurrence, wherein the neural activity pattern is the analysis representation of the audio signal;
   a coupler arranged to output the neural activity pattern to a plurality of nerve fibers of a human patient as electrical and/or chemical excitations; wherein
   the converter for converting the audio signal includes:
      a converter for converting the audio signal into a representation describing a movement of a basilar membrane in the ear model;
      a converter for converting the representation describing the movement of a basilar membrane into a representation describing a deflection of a stereocilium of a hair cell coupled to the basilar membrane; and
      a converter for converting the representation describing the deflection of the stereocilium into a representation describing the neurotransmitter vesicle occurrence;
   the converter for converting the representation describing the movement of the basilar membrane into the representation describing the deflection of a stereocilium is implemented to describe the stereocilium by a model of a harmonic oscillator which comprises a spring return force and an attenuation based on a laminar flow resistance;

a spring constant D which describes a connection between the spring return force and the deflection of the stereocilium lies in a range between $1 \times 10^{-3}$ N/m and $6 \times 10^{-3}$ N/m; and the device for analyzing the audio signal comprises a hardware implementation, or the device for analyzing the audio signal is implemented using a computer.

4. A method for analyzing an audio signal to acquire an analysis representation of the audio signal, comprising:

converting the audio signal into a representation representing a neurotransmitter vesicle occurrence in clefts between a plurality of nerve fibers and inner auditory cells of an ear model;

calculating a neural activity pattern over time on the plurality of nerve fibers resulting based on the neurotransmitter vesicle occurrence, wherein the neural activity pattern is the analysis representation of the audio signal; and outputting, by a coupler, the neural activity pattern to a plurality of nerve fibers of a human patient as electrical and/or chemical excitations; wherein converting the audio signal includes converting the audio signal into a representation describing a movement of a basilar membrane in the ear model, converting the representation describing the movement of a basilar membrane into a representation describing a deflection of a stereocilium of a hair cell coupled to the basilar membrane, and converting the representation describing the deflection of the stereocilium into a representation describing the neurotransmitter vesicle occurrence;

converting the representation describing the movement of the basilar membrane into the representation describing the deflection of a stereocilium is implemented to describe the stereocilium by a model of a harmonic oscillator which comprises a spring return force and an attenuation based on a laminar flow resistance;

the model of the harmonic oscillator is implemented so that an excitation of the harmonic oscillator takes place by a second force component $F_{stoch}$ which describes a stochastic thermal force; and the converting the audio signal and the calculating the neural activity pattern over time are performed by a hardware implementation or using a computer.

5. A method for analyzing an audio signal to acquire an analysis representation of the audio signal, comprising:

converting the audio signal into a representation representing a neurotransmitter vesicle occurrence in clefts between a plurality of nerve fibers and inner auditory cells of an ear model;

calculating a neural activity pattern over time on the plurality of nerve fibers resulting based on the neurotransmitter vesicle occurrence, wherein the neural activity pattern is the analysis representation of the audio signal; and outputting, by a coupler, the neural activity pattern to a plurality of nerve fibers of a human patient as electrical and/or chemical excitations; wherein converting the audio signal includes converting the audio signal into a representation describing a movement of a basilar membrane in the ear model, converting the representation describing the movement of a basilar membrane into a representation describing a deflection of a stereocilium of a hair cell coupled to the basilar membrane, and converting the representation describing the deflection of the stereocilium into a representation describing the neurotransmitter vesicle occurrence;

converting the representation describing the movement of the basilar membrane into the representation describing the deflection of a stereocilium is implemented to describe the stereocilium by a model of a harmonic oscillator which comprises a spring return force and an attenuation based on a laminar flow resistance;

the model of the harmonic oscillator is described by a movement equation of the following form:

$$m\ddot{x} = -Dx - K\dot{x} + F_{ext}(t) + F_{stoch}(t)$$

wherein $-Dx$ represents a spring return force;
wherein $-K\dot{x}$ represents a laminar flow resistance;
wherein $F_{ext}$ represents an external force, which is proportional to a velocity v(t) of the basilar membrane; and
wherein $F_{stoch}$ represents a stochastic thermal force by an impact movement of atoms; and the converting the audio signal and the calculating the neural activity pattern over time are performed by a hardware implementation or using a computer.

6. A method for analyzing an audio signal to acquire an analysis representation of the audio signal, comprising:

converting the audio signal into a representation representing a neurotransmitter vesicle occurrence in clefts between a plurality of nerve fibers and inner auditory cells of an ear model;

calculating a neural activity pattern over time on the plurality of nerve fibers resulting based on the neurotransmitter vesicle occurrence, wherein the neural activity pattern is the analysis representation of the audio signal; and outputting, by a coupler, the neural activity pattern to a plurality of nerve fibers of a human patient as electrical and/or chemical excitations; wherein converting the audio signal includes converting the audio signal into a representation describing a movement of a basilar membrane in the ear model, converting the representation describing the movement of a basilar membrane into a representation describing a deflection of a stereocilium of a hair cell coupled to the basilar membrane, and converting the representation describing the deflection of the stereocilium into a representation describing the neurotransmitter vesicle occurrence;

converting the representation describing the movement of the basilar membrane into the representation describing the deflection of a stereocilium is implemented to describe the stereocilium by a model of a harmonic oscillator which comprises a spring return force and an attenuation based on a laminar flow resistance;

a spring constant D which describes a connection between the spring return force and the deflection of the stereocilium lies in a range between $1 \times 10^{-3}$ N/m and $6 \times 10^{-3}$ N/m; and the converting the audio signal and the calculating the neural activity pattern over time are performed by a hardware implementation or using a computer.

7. A non-transitory computer-readable medium comprising a program code for performing a method according to claim 4 when the computer program runs on a computer.

8. A non-transitory computer-readable medium comprising a program code for performing a method according to claim 5 when the computer program runs on a computer.

9. A non-transitory computer-readable medium comprising a program code for performing a method according to claim 6 when the computer program runs on a computer.

* * * * *